(12) United States Patent
Verbruggen et al.

(10) Patent No.: US 8,532,362 B2
(45) Date of Patent: Sep. 10, 2013

(54) SCORING SYSTEM TO MONITOR NATURAL OR DRUG-MODIFIED DISEASE PROGRESSION IN "EROSIVE OSTEOARTHRITIS" OF THE INTERPHALANGEAL FINGER JOINTS

(75) Inventors: August Verbruggen, Nazareth (BE); Ruth Wittoek, Laarne (BE); Bert Vander Cruyssen, Bornem (BE); Dirk Elewaut, Heusden (BE)

(73) Assignee: Ghent University, Ghent (BE)

( * ) Notice: Subject to any disclaimer, the term of this patent is extended or adjusted under 35 U.S.C. 154(b) by 402 days.

(21) Appl. No.: 13/055,485

(22) PCT Filed: Jul. 24, 2009

(86) PCT No.: PCT/EP2009/059609
§ 371 (c)(1),
(2), (4) Date: Mar. 25, 2011

(87) PCT Pub. No.: WO2010/010193
PCT Pub. Date: Jan. 28, 2010

(65) Prior Publication Data
US 2011/0263948 A1    Oct. 27, 2011

(30) Foreign Application Priority Data

Jul. 24, 2008 (GB) .................................. 0813518.8
Sep. 1, 2008 (GB) .................................. 0815857.8

(51) Int. Cl.
*G06K 9/00* (2006.01)

(52) U.S. Cl.
USPC ............................ 382/132; 382/128; 600/407

(58) Field of Classification Search
USPC .................................. 382/128, 132; 600/407
See application file for complete search history.

(56) References Cited

U.S. PATENT DOCUMENTS

| | | | | |
|---|---|---|---|---|
| 5,193,106 | A * | 3/1993 | DeSena ......................... | 378/163 |
| 7,184,814 | B2 * | 2/2007 | Lang et al. ..................... | 600/416 |
| 7,778,453 | B2 * | 8/2010 | Camus et al. .................. | 382/128 |
| 7,796,791 | B2 * | 9/2010 | Tsougarakis et al. .......... | 382/128 |

FOREIGN PATENT DOCUMENTS

EP    1046374 A1    10/2000

OTHER PUBLICATIONS

Duryea et al., "Neural network based automated algorithm to identify joint locations on handŌwrist radiographs for arthritis assessment", Med. Phys. 29 (3), Mar. 2002, 403-411.*
Goligher et al., "Radiographic Joint Space Width in the Fingers of Patients With Rheumatoid Arthritis of Less Than One Year's Duration", Arthritis & Rheumatism, vol. 54, No. 5, May 2006, pp. 1440-1443.*
Kauffman et al., "Detection of joint space narrowing in hand radiographs", Medical Imaging 2006: Image Processing, Proc. of SPIE vol. 6144, 614446-1-614446-11.*
Angwin et al., "Reliabiilty and Sensitivity of Joint Space Measurements in Hand Radiographs Using Computerized Image Analysis", The Journal of Rheumotology 28:8, pp. 1825-1836, 2001.

(Continued)

*Primary Examiner* — David Zarka
*Assistant Examiner* — Katrina Fujita
(74) *Attorney, Agent, or Firm* — Dinsmore & Shohl LLP

(57) ABSTRACT

The present invention provides a scoring system to monitor natural or drug-modified disease progression in erosive interphalangeal finger joint osteoarthrits and the use of said scoring system to identify and value drugs with anticatabolic and/or repair promoting potential.

17 Claims, 10 Drawing Sheets

(56) References Cited

OTHER PUBLICATIONS

Bottcher et al., Digital X-Ray Radiogrammetry Combined with Semiautomated Analysis of Joint Space Widths as a New Diagnostic Approach in Rheumatoid Arthritis, Arthritis & Rheumatism, vol. 52, No. 12, pp. 3850-3859, Dec. 2005.

Buckland-Wright et al., "Quantitative Microfocal Radiographic Assessment of Disease and Progression in Osteoarthritis of the Hand", Journal of Rheumotology (Supplemental 27), vol. 18, 1991.

Buckland-Wright, "Subchondral bone changes in hand and knee osteoarthritis detected by radiology", Osteoarthritis and Cartilage 12, S10-S19, 2004.

Finckh et al., "Performance of an Automated Computer-Based Scoring Method to Assess Joint Space Narrowing in Rheumatoid Arthritis", Arthritis & Rheumatism, vol. 54, No. 5, pp. 1444-1450, May 2006.

Maheu et al., "Design and conduct of clinical trials in patients with osteoarthritis of the hand: recommendations from a task force of the Osteoarthritis Research Society International", Osteoarthritis and Cartilage 14, pp. 303-322, 2006.

Patel et al., "Advancement in the zone of calcified cartilage in osteoarthritic hands of patients detected by high definition macroradiology", Osteoarthritis and Cartilage 7, pp. 520-525, 1999.

Pfeil et al., "Computer-aided joint space analysis of the metacarpal-phalangeal and proximal-interphalangeal finger joint: normative age-related and gender-specific data", Skeletal Radiology 36, pp. 853-864, 2007.

Ravaud et al., "Assessing Smallest Detectable Change Over Time in Continuous Structural Outcome Measures: Application to Radiological Change in Knee Osteoarthritis", J Clin Epidemiol vol. 52, No. 12, pp. 1225-1239, 1999.

Sharp et al., "Computer-Based Methods for Measuring Joint Space and Estimating Erosion Volume in the Finger and Wrist Joints of Patients with Rheumatoid Arthritis", Arthritis & Rheumatism, vol. 43, No. 6, pp. 1378-1386, Jun. 2000.

Van't Klooster et al., "Automatic quantification of osteoarthritis in hand radiographs: validation of a new method to measure joint space width", Osteoarthritis and Cartilage 16, pp. 18-25, 2008.

Verbruggen et al., "Numerical Scoring Systems for the Anatomic Evolution of Osteoarthritis of the Finger Joints", Arthritis & Rheumatism, vol. 39, No. 2, pp. 308-320, Feb. 1996.

Verbruggen et al., "Chondroitin sulfate: S/DMOAD (structure/disease modifying anti-osteoarthritis drug) in the treatment of finger joint OA", Osteoarthritis and Cartilage 6 (supplement A), pp. 37-38, 1998.

Verbruggen et al., "Systems to Assess the Progression of Finger Joint Osteoarthritis and the Effects of Disease Modifying Osteoarthritis Drugs", cLINICAL rHEUMATOLOGY 21, pp. 231-243, 2002.

Verbruggen et al., "An Optimized Scoring System (Guss TM) for Erosive OA of the Interphalangeal Finger Joints allows Quantifying Destruction and Repair of Connective Tissues", Poster Presentations—Imaging, p. S181.

Zhang et al., "EULAR evidence-based recommendations for the diagnosis of hand osteoarthritis: report of a task force of ESCISIT", Ann Rheum Dis; 68, pp. 8-17, 2009.

PCT/EP2009/059609 International Preliminary Report on Patentability dated Jun. 24, 2010.

* cited by examiner

SCORING SYSTEM TO MONITOR NATURAL OR DRUG-MODIFIED DISEASE PROGRESSION IN "EROSIVE OSTEOARTHRITIS" OF THE INTERPHALANGEAL FINGER JOINTS

The present invention provides a scoring system to monitor natural or drug-modified disease progression in erosive interphalangeal finger joint osteoarthritis and the use of said scoring system to identify and value drugs with anticatabolic and/or repair promoting potential.

BACKGROUND OF THE INVENTION

In most 'hand osteoarthritis (OA)' surveys, a number of subjects is discerned with the clinics of erosive finger joint OA (Zhang W et al, EULAR ESCISIT group, 2008). These patients show symmetrical and severe destructive changes in more than a few of their interphalangeal (IP) joints. The progressive nature of this disease has been well documented (Verbruggen G, Veys E M, 1996).

In these IP joints the classical picture of 'non-erosive' OA is complicated by manifest erosive changes, which precede a period in which repair phenomena in the 'eroded' finger joints lead to the generation of a new subchondral plate covered by cartilaginous tissue. On the roentgenpicture the erosive changes in the affected IP joints include the disappearance of the joint space within a relatively short period of time. Concurrently with or shortly after the disappearance of the articular cartilage, substantial osteolytic areas may emerge in the subchondral bone and the subchondral plate becomes eroded. The joint space of the affected IP joint may then appear enlarged and utterly disordered. These destructive phases are always followed by repair or remodeling. Then, new irregular sclerotic subchondral plates are formed, and in between these, a new joint space becomes visible. The subchondral osteolytic areas gradually disappear. Huge osteophytes are formed during this phase. No further evolution is seen in remodeled IP joints.

In osteoarthritis, which is a degenerative joint disease, endogenous disease promoting factors are released in a dense extracellular matrix surrounding the chondrocyte. This dense extracellular matrix makes it almost impossible for therapeutics (e.g. antibodies or receptor antagonists) to scavenge this endogenous disease promoting factors before they reach their target. In contrast, in inflammatory joint diseases such as rheumatoid arthritis, exogenous factors (like TNF □) are released from an inflamed synovium and therapeutics (anti-TNF monoclonal antibodies or receptor antagonists) will scavenge these exogenous factors before they reach the articular cartilage cell to provoke an autodestructive (IL-1) cascade.

5-10% of subjects with "erosive hand" osteoarthritis (OA) show severe destructive changes in their interpalangeal (IP) finger joints.

The classical picture of 'non-erosive' OA in these IP joints is complicated by destructive changes before naturally occurring repair in the 'eroded' finger joints leads to the generation of new remodeled articular tissues. The 3 anatomical structures in the IP finger joints: the subchondral bone, the subchondral bone plate and the synovial joint space are affected in a way distinguishing the radiographic picture from that of other destructive rheumatic joint diseases, e.g. psoriatic or rheumatoid arthritis. Also, the radiographic picture is absolutely different from that of the classic forms of osteoarthritis.

Assessing abnormalities radiologically is one of the most powerful means available to the clinical investigator. Radiographs, which serve as a permanent record of disease progression at different times, can be compared simultaneously. A set of radiographs from individual patients can be "blinded" and randomly assigned a sequence, to achieve greater objectivity in scoring. Standardized patient positioning and radiographic techniques, as well as the use of fine-detail screen-film combinations, have also improved the sensitivity and reproducibility of radiographic scoring.

Recently, the digital imaging techniques have been applied to the study of bone and joint disease. Improvements in hardware and software for digital image workstations have led to the development of a number of picture archiving and communication systems, which have been reported to increase clinical efficiency and are now well accepted by radiologists. The advantages of digital image formats are facilitated archiving and retrieval, image processing and display and remote transmission.

EP1046374 published on 25 Oct. 2000, describes "the Promosco X-posure System" to determine Bone Mineral Density (BMD) using radiogrammetry. Where BMD measures are particularly useful in diagnosing osteoporosis, it has no predictive power as to disease progression and/or in monitoring treatment response in arthritic conditions.

A publication of Sharp J. T. et al. (2000) relates to the feasibility of using computer programs to measure the radiographic joint space width and estimate erosion volumes in the hands of patients with rheumatoid arthritis (RA).

In a publication of Böttcher J. et al. (2005) the above mentioned "the Promosco X-posure System" has been complemented with a semi-automated analysis of Joint Space Width (JSW) as a new diagnostic approach in RA.

An article of Finckh A. et al. (2006) provides an alternative algorithm to determine JSW in RA.

Hence, for RA there are several scoring systems available that determine the RA lesions. However, these systems are unable to score osteochondral repair in synovial joints after e.g. anti-inflammatory treatment of subjects with RA.

A publication of Van 't Klooster R. et al (2008) provides an automatic measurement of the joint space width in finger joints in hand radiographs, to quantify OA in forty subjects with primary non-erosive OA. Buckland-Wright C. et al (1991, 1999 and 2004) uses radiography to detect changes in subchondral bone and the advancement in the zone of calcified cartilage that occur with the onset and progression of hand OA. These last documents each give methods that focus on different aspects of non-erosive OA and are unable to reflect or score disease onset and progression typical for erosive OA of the interphanlangeal finger joints.

Verbruggen G et al (1998, 2002) provides a system to score the progression of hand erosive OA based on consecutive pathological phases recognized in the course of the disease: A stationary or "S" phase OA joint (a non-erosive OA joint) can enter the phase where the joint space has disappeared (the "J" phase). Then the OA joint can progress to the phase where manifest erosive changes have occurred (the "E" phase), followed by the final repair/remodeling or "R" phase. In this scoring system numerical values were attributed to the different phases and the system only allowed to record a change from one pathological phase to the other over a substantial 3 year period of time (Verbruggen G et al, 1998, 2002). This analytical system did not allow discriminating between smaller changes in anatomical progression e.g. within the same pathological phase.

However, destruction and reconstruction of the subchondral bone, the subchondral bone plate and the synovial joint space in the IP finger joints can show considerable variation in morbidity and can be observed through all the successive pathological phases of erosive OA. Considerable overlap of destruction and repair can occur in the succeeding phases of the disease.

Hence, for erosive hand OA there is a need for an appropriate scoring system that is able to quantify disease progression especially early in the course of the disorder and that can assess the reparative changes after drug treatment or in the late stages of the disease and thus can score disease progression or repair in shorter follow-up periods.

The present invention solves the above described problems.

Grading the presence of normal tissue in at least 3 well-defined tissue compartments (subchondral bone plate, subchondral bone and joint space) on a stepwise or continuous incremental scale and summation of these at least 3 subdomain scores allows to generate an overall score for an IP finger joint in whichever phase of the disease. The scoring method is significantly sensitive to changes over time and allows changes in IP joint scores in small study populations to be calculated over short follow-up times. The scoring system is particularly valuable to monitor natural or drug-modified disease progression in erosive interphalangeal finger joint OA. Furthermore it can serve as a clinical tool to identify and value drugs with anticatabolic and/or repair promoting potential in erosive interphalangeal finger joint OA.

SUMMARY OF THE INVENTION

The invention provides a method to monitor disease progression in a subject with erosive osteoarthritis of the interphalangeal finger joints characterized by determining the following three variables the amount of normal tissue of the subchondral bone, the amount of normal tissue of the subchondral bone plate, and the presence of a normal joint space on a series of at least two consecutive radiographs of the same interphalangeal finger joint of said subject.

In an embodiment of the invention, the method further comprises determining as a fourth variable the width of the joint.

In a further embodiment of the invention, the series of the at least two consecutive radiographs are taken within a time interval of at least six months.

In another embodiment of the invention the interphalangeal finger joint can be a distal and/or a proximal interphalangeal joint.

In yet a further embodiment of the invention the variables are indicated manually or automatically as a surface or a line and/or can be translated in numerical scores.

In yet another embodiment of the invention the numerical scores of the amount of normal tissue of the subchondral bone, the amount of normal tissue of the subchondral bone plate, and the presence of a normal joint space are recorded on a stepwise or continuous incremental scale ranging from 0 to 100 and/or the sum of the numerical scores gives an overall numerical score per interphalangeal finger joint of said subject.

In an aspect of the invention, a decrease in the overall numerical score is indicative for destruction of said interphalangeal finger joint and an increase in the overall numerical score is indicative for remodeling/repair of said interphalangeal finger joint.

A further aspect of the invention provides the use of the above-defined methods to monitor natural or drug-modified disease progression in a subject with erosive osteoarthritis of the interphalangeal finger joints.

Yet a further aspect of the invention provides the use of the above-defined methods to identify or evaluate the effects of a drug. Said drug can have anticatabolic or repair promoting effects.

A last embodiment of the invention provides the use of the method to determine a method of treatment for the subject with erosive osteoarthritis of the interphalangeal finger joints.

DETAILED DESCRIPTION

Figure 3:
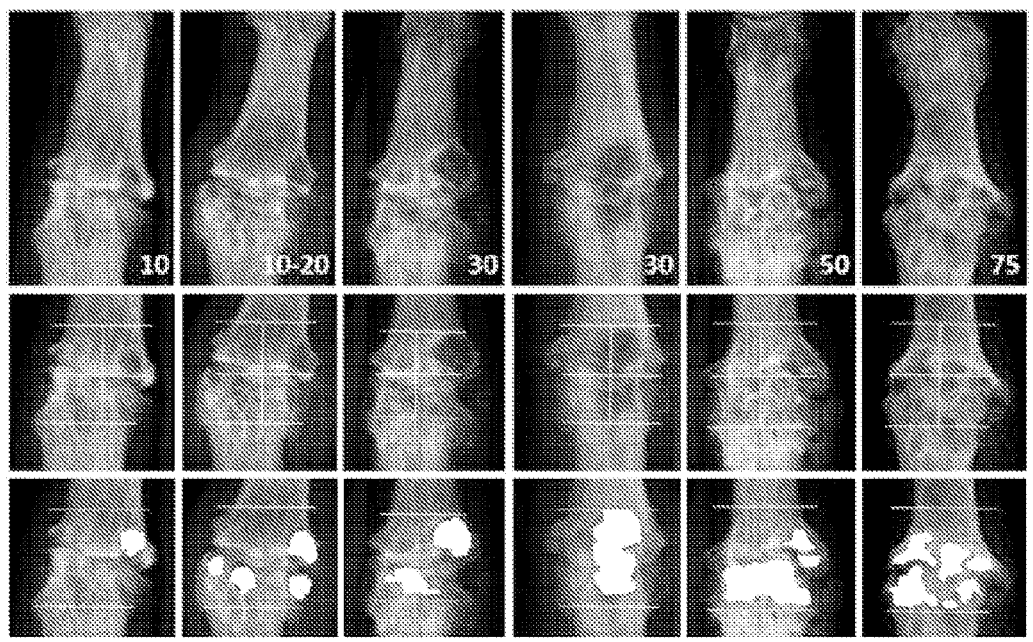
FIG. 3: The amount of normal tissue of the subchondral bone. Top: series of pictures with increasing osteolytic areas. The radiographs were collected from 6 different proximal interphalangeal (PIP) joints. Percentages of pathological bone tissue in the area of interest are given. Middle: the area of interest is defined as the rectangular square of which the side equals the width of the joint space. Bottom: pathological osteolytic zones can be defined manually to facilitate computing.

Definitions:

With the term "the amount of normal tissue of the subchondral bone" is meant the proportions of the subchondral bone area with bone architecture in a rectangular square of which the height equaled the width of the joint space, and the length at least equaled the width of the entire joint. The joint space is positioned in the centre of this square (see FIG. 3). As shown in more detail in the examples hereinafter, the area with bone architecture is meant to include all area excluding the radiotranslucent area within the aforementioned square. As used herein, the radiotranslucent area within the aforementioned square, is meant to include all area where osteolytic activity and remodelling caused a disarrangement of the trabecular pattern, or where a complete loss of the trabecular structure had occurred.

For example, in case digitized radiographs are used, the area of the aforementioned square corresponds to a number of pixels having 256 pixel values ranging from 0 (black) to 255 (white). In one method, according to the present invention to determine the translucent area within said square, the mean pixel value±SEM of the translucent area surrounding the interphalangeal finger joint is taken as a reference, and the sum of all pixels having a pixel value within said range is scored as the translucent area within said square. Alternatively a fixed range of pixel tolerance is applied, and typically is between and about the pixel value at the translucent area surrounding the interphalangeal finger joint±and about 10, 15, 20, or 25; in particular ±and about 20. In a further embodiment according to the present invention, an electronic ruler and point tool may be used to define the translucent area within the aforementioned square. In said embodiment the translucent pixel value corresponds to the average pixel value with said defined translucent area, and the range used to score the number of pixels within said defined area is either the SEM or a fixed range of pixel tolerance as defined hereinbefore. Alternatively, the pixels present within the defined translucent area are given a fixed and predetermined pixel value (for example 83). In said embodiment the translucent pixel value T in the formula hereinafter, corresponds to said predetermined pixel value and the range in pixel tolerance (R) equals 0.

The amount of normal subchondral bone tissue is accordingly represented as;

$$A_{sb}(\%) = 100 \times \left(1 - \frac{\#Pix_{[<T>\pm R]}}{\#Pix_{sq}}\right)$$

wherein; $A_{sb}$=the area of subchondreal bone tissue $Pix_{[<T>\pm R]}$=Pixels having a pixel value equal to T or within the range set by R, wherein T represents the translucent pixel value and R represents the range of pixel values described hereinbefore, i.e. either set as the SEM of T or as a predetermined tolerance.

$Pix_{sq}$=the total number of pixels found within the square of which the height equaled the width of the joint space, and wherein the joint space is positioned in the centre of said square.

Within the methods of the present invention, the square of which the height equals the width of the joint space, and wherein the joint space is positioned in the centre of said square, is set as a readily recognizable bone and joint anatomic feature common to all interphalangeal finger joints. It sets a landmark for the area of interest to allow and determine the amount of the aforementioned variables in an accurate and reproducible manner.

Figure 4:
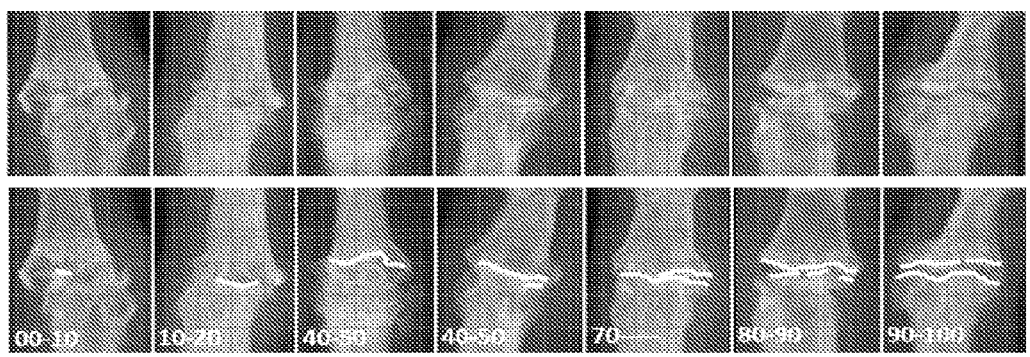
FIG. 4: The amount of normal tissue of the subchondral bone plate. The radiographs were collected from 7 different PIP joints. Top: series of pictures with increased proportions of reconstructed subchondral bone plate. Bottom: Proportions of a regular relatively smooth supporting bone plate flanking the joint space were defined manually. Percentages of subchondral bone plate that reappeared are given.

With the term "the amount of normal tissue of the subchondral bone plate" is meant the proportion of the subchondral bone plate with a regular radioopaque linear structure within the position of the original joint space (see FIG. 4), compared to a line in the centre of the aforementioned square, said line having twice the length of the joint space, in other words having twice the height of said rectangle.

For example, in case digitized radiographs are used, the line having twice the length of the joint space, in other words having twice the height of said rectangle represents the reference value to determine the amount of subchondral bone plate. As will be evident to the skilled artisan, the width of said line should equal the width of the regular radioopaque linear structure corresponding to the subchondral bone plate within the aforementioned square. In one method, according to the present invention, said regular radioopaque linear structure is marked under the users guidance with an electronic ruler to the selected digital image. The number of pixels in the thus obtained subchondreal bone plate line marking is representative for the amount of subchondral bone plate structure present within the aforementioned square and normalized vis-á-vis the aforementioned reference value. In an alternative embodiment, art known pattern recognition techniques and edge detection techniques are used to define and select the pixels representing the regular radioopaque linear bone plate structures within the aforementioned square. In an even further embodiment, a data set defining a reference pixel value for the subchondral bone plate is used to determine the number of pixels corresponding to the subchondral bone plate structure present within the aforementioned square. As for the subchondral bone above, said reference pixel value is applied within a range corresponding to the SEM or a fixed pixel tolerance of between and about 2, 3, 4, 5, 6, 7, 8, 9, 10, or 15; in particular ±and about 5.

The amount of normal tissue of the subchondral bone plate is accordingly represented as;

$$A_{bp}(\%) = 100 \times \frac{(\#Pix_{sblm})}{\#Pix_{sbrl}}$$

wherein; $A_{bp}$=the amount of normal subchondral bone plate

$Pix_{sblm}$=the amount of pixels of the subchondral bone plate line marking, wherein said pixels are either set using a user guided electronic ruler, using automatic pattern recognition techniques and/or edge detection techniques, or using a predefined reference pixel value for the subchondral bone plate structure.

$Pix_{sbrl}$=the total number of pixels found within the subchondral bone plate reference line, wherein the length of said line corresponds to twice the twice the height of said rectangle, and wherein the width of said line corresponds to the width of the subchondral bone plate line marking.

Figure 5:
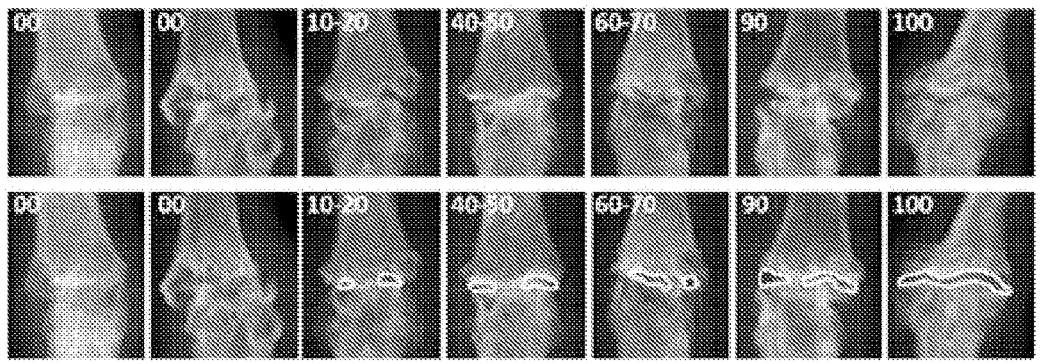
FIG. 5: The presence of a normal joint space. The radiographs were collected from 7 different PIP joints. Top: series of pictures with increased proportions of reappearing joint space. Percentages of subchondral bone plate that had reappeared are given. Bottom: Proportions of radiotranslucent area bordered with 2 subchondral plates were defined and depicted manually. In the IP joint on the second picture of this series, the translucent zone in between the 2 bone endings of this IP joint is not considered as a joint space as this translucent zone is not bordered by 2 subchondral plates.

With the term "the presence of a normal joint space" is meant the proportion of the joint width with a radiotranslucent area bordered with 2 subchondral plates (see FIG. 5). Within the area of interest, the subchondral plates are marked using the subchondral bone plate marking (supra). The translucent area bordered (flanked) by said subchondral bone plate marking is marked under the users guidance with an electronic ruler to the selected digital image. The cumulative length or the number of pixels in the thus obtained joint space line markings is representative for the amount of joint space present within the aforementioned square. In said embodiment, the landmark or reference to determine the aforementioned proportion consists of a line in the centre of the rectangular square (supra), wherein the length of said line corresponds to the height of said rectangle (supra). When applied on digitized images, the width of said joint space reference line should equal the width of the joint space line marking The amount of normal joint space is accordingly represented as;

$$A_{js}(\%) = 100 \times \frac{(\#Pix_{tajs})}{\#Pix_{jsrl}}$$

wherein; $A_{js}$=the amount of normal joint space

$Pix_{tajs}$=the amount of pixels of the translucent area bordered (flanked) by subchondral bone plate marking, either taken as a whole or as the number of pixels in a joint space line marking (supra)

Figure 6:
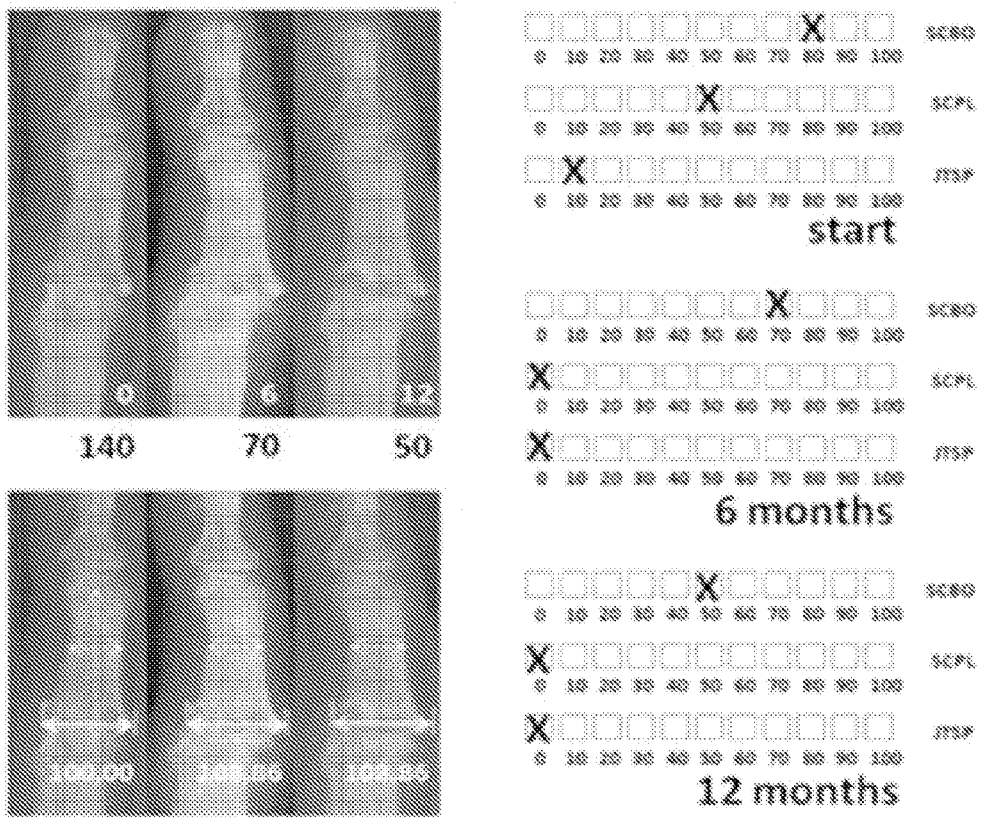
FIG. 6: The width of the joint. Top: Radiographs taken with 6-month intervals. Bottom: Changes in joint width (straight line arrow) of a PIP joint, relative to the diameter of the mid diaphysis of the intermediate phalange (dotted line arrow). Joint width increased with 8.86% during the first 6 months of follow-up. No further increase in joint width is seen during a next 6-month period.

$Pix_{jsrl}$=the total number of pixels found within the joint space reference, wherein the reference is either a plane or a line in the centre of the rectangle square, having a length that corresponds to the height of said rectangle, and a width that equals either the width of the translucent area above or the width of the joint space line marking With the term "the width of the joint" is meant the proportion of joint width of the distal and proximal IP joints, relative to the diameter of the diaphysis of the flanking intermediate phalange (see FIG. 6).

Description:

Previously, a system to score the progression of hand OA was described based on the consecutive pathological phases recognized in the course of the disease (Verbruggen G et al, 1998, 2002): a non-erosive OA joint ("S" or stationary OA joint) could enter the "J" phase when the joint space had disappeared, and then the "E" phase when manifest erosive changes had occurred. Next, the "R" phase wherein repair and remodeling occurs, would ensue.

Numerical values were attributed to the different phases and the system then allowed to record a change from one pathological phase to the other over a substantial 3 year period.

For the present invention, radiographic data were obtained in 60 patients with erosive IP OA. Patients were followed for 1 year. Posteroanterior radiographs of the hands were obtained at the start of this study and after 6 and 12 months. Pictures typical and distinctive for the erosive "E" and remodeled "R" anatomical phases, as defined in the previously described scoring system, showed considerable variation in morbidity. Also destructive events and remodeling in these finger joints showed considerable overlap. Remodeling of these IP joints occurred much more rapidly than previously recognized. Pertinent changes could be observed within 6-month periods of follow-up.

Hence, changes can be observed on at least two consecutive radiographs. More in particular changes can be observed on 2, 3, 4, 5 or more consecutive radiographs.

Changes typical for the destructive events in the "E" target joints are:

1: disappearance of the joint space (FIG. 1B, C); either by the loss of the articular cartilage or by the destruction of the subchondral bone plate 2: destruction of the subchondral bone plate (FIGS. 1A, B); osteolytic events in and near the subchondral plate lead to a ruffled aspect of the subchondral plate.

Figure 1:
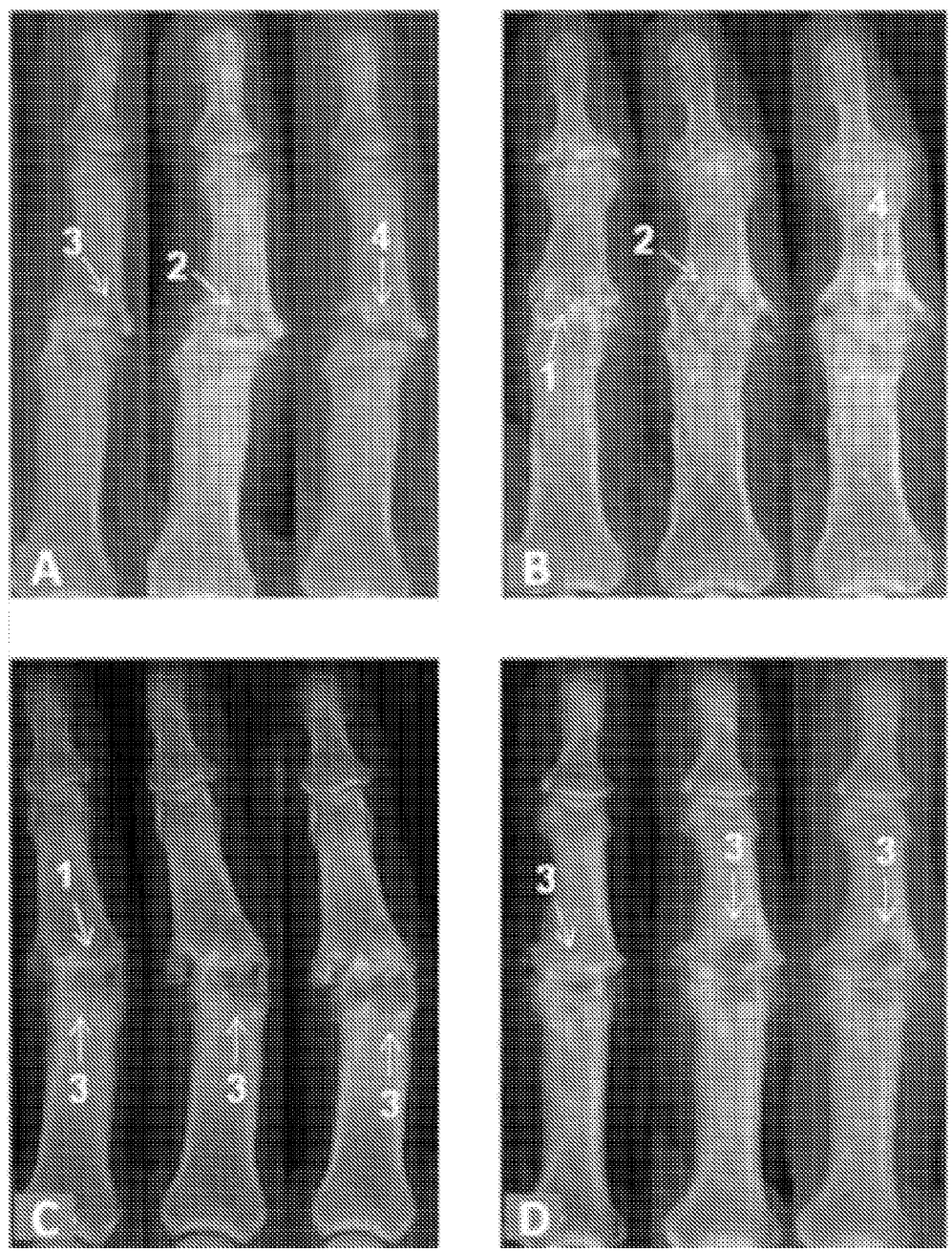
FIG. 1: A-D. Erosive changes in IP joints occurring during 12-months follow-up: 1. disappearance of the joint space. 2. Destruction of the subchondral bone plate; osteolytic events in and near the subchondral plate lead to a ruffled aspect of the subchondral plate. 3. Appearance of osteolytic areas in the subchondral bone. 4. Both the destruction of the subchondral plate and the osteolytic events in the subchondral bone area cause the generation of a widened pseudo-joint space with irregular margins.

3: appearance of osteolytic areas in the subchondral bone (FIGS. 1A, C, D).

4: the generation of a widened space-joint with irregular margins (FIGS. 1A, B); by both the destruction of the subchondral plate and the osteolytic events in the subchondral bone area.

Figure 2:
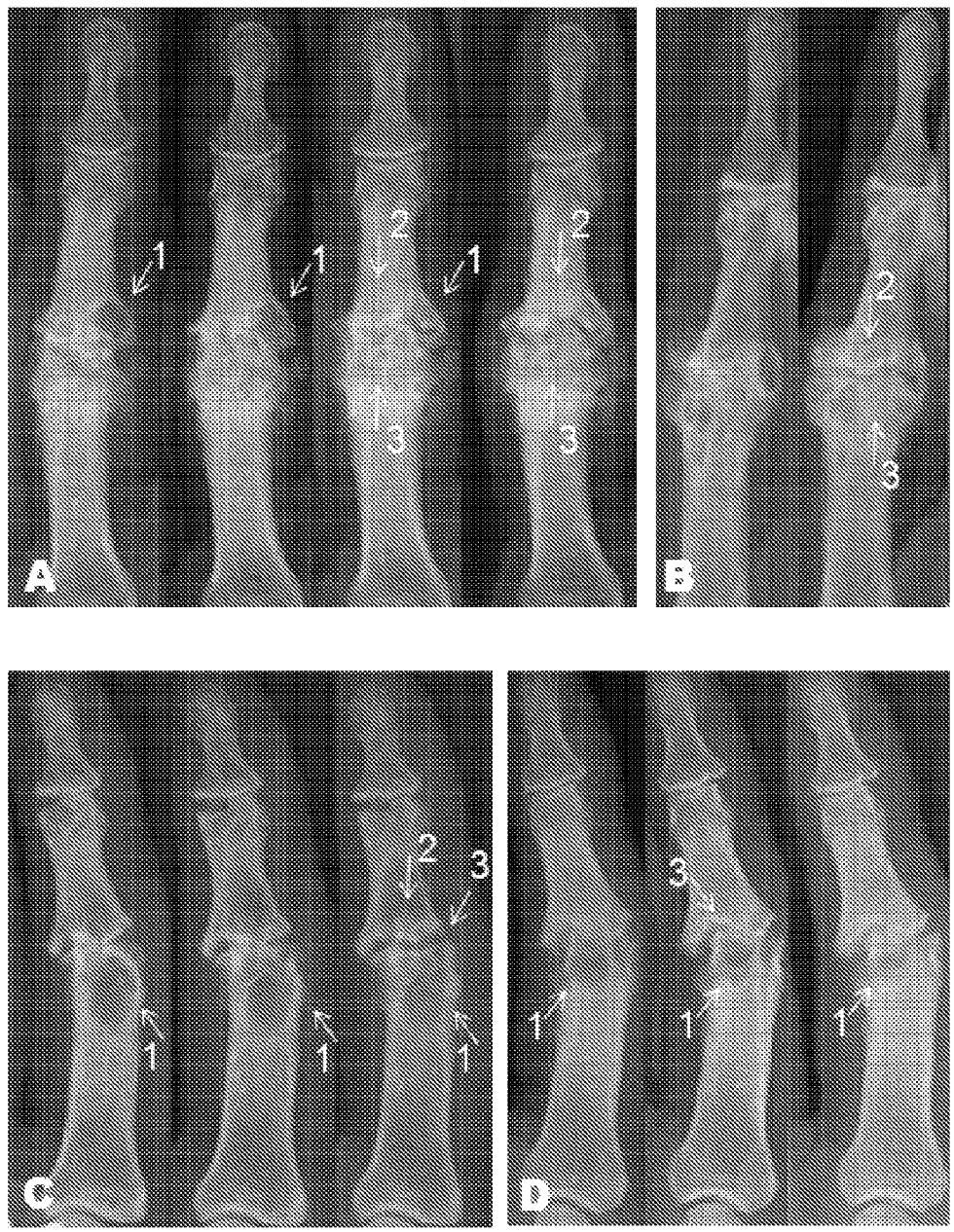
FIG. 2: A-D. Remodeling of IP joints observed on radiograms taken with 6-month intervals: 1. disappearance of the osteolytic areas in the subchondral bone area. 2. Reconstruction of the subchondral bone plate which did not necessarily appear as a denser radioopaque zone. 3. Reappearance of a radiotranslucent area recognized as the reconstructed joint space.

Changes typical for the remodeling and repair of the affected tissues in "E" or "R" target joints are:
1. disappearance of the osteolytic areas in the subchondral bone area (FIGS. 2 A, C, D) and the proportions of ordinary subchondral bone area thus recovered.
2. reconstruction of the subchondral bone plate (FIGS. 2 A, B, C); which did not necessarily appear as a denser radioopaque zone.
3. reappearance of a radiotranslucent area recognized as the reconstructed joint space (FIG. 2 A-C).

From these observations, the following three variables were retained to grade the severity of the changes on the radiograms.
the amount of normal tissue of the subchondral bone,
the amount of normal tissue of the subchondral bone plate, and
the presence of a normal joint space.

It is accordingly a first objective of the present invention to provide a measuring system for a radiograph of an interphalangeal finger joint characterized in having means to determine as variables;
the amount of normal tissue of the subchondral bone,
the amount of normal tissue of the subchondral bone plate, and
the amount of a normal joint space
on a series of at least two consecutive radiographs of the same interphalangeal finger joint of said subject.

The measuring system of the present invention is designed to be applied on either digitized radiographs or preferably with digital forms of Computer Radiography or Direct Radiography. In either case the system of the present invention includes an image acquisition device to capture or convert the radiographs as digital input to the system.

Once captured into the system, the image is subjected to the selection of area(s) of interest on the radiograph, hereinafter also referred to as 'landmarks', that allow determining the aforementioned variables. Means to determine the variables accordingly include manual or automatic input means to select prescribed landmarks on each digital image as a surface or a line.

In the method of the present invention, the location of landmarks is currently a task that must be undertaken by an individual. That is, the individual selects several landmarks as defined herein, that are visible on each of the two images, and enters the coordinates (manually, by a touch screen or with a mouse click) of each landmark on each x-ray image. It will be understood, however, that the landmarks as defined herein, may also be recognized by appropriate computer software, and similar results obtained. For example, artificial neural networks (ANN) can also be applied to the differentiation of landmarks on each x-ray image. ANN is a non-algorithmic approach to information processing. Unlike many artificial intelligence techniques, which require extensive knowledge of the many parameters involved, ANNs learn directly from examples that are provided repeatedly. Once trained, a neural network can distinguish among input patterns on the basis of its learning experience.

A first landmark selected on the radiographs using the input means of the aforementioned system, allows to determine the amount of normal tissue of the subchondral bone, and consists of a rectangular square of which the height equals the width of the joint space; wherein the joint space is positioned in the centre of this square; and wherein the proportion of the subchondral bone area with normal-looking bone architecture is indicative for the amount of normal tissue of the subchondral bone. Accordingly, in a further aspect, the system comprises computational means to calculate the amount of normal tissue of the subchondral bone as;

$$A_{sb}(\%) = 100 \times \left(1 - \frac{\#Pix_{[<T>\pm R]}}{\#Pix_{sq}}\right)$$

wherein; $A_{sb}$=the area of subchondreal bone tissue
$Pix_{[<T>\pm R]}$=Pixels having a pixel value equal to T or within the range set by R, wherein T represents the translucent pixel value and R represents the range of pixel values described hereinbefore, i.e. either set as the SEM of T or as a predetermined tolerance.
$\#Pix_{sq}$=the total number of pixels found within the square of which the height equaled the width of the joint space, and wherein the joint space is positioned in the centre of said square.

A second set of landmarks using the input means of the aforementioned system, allows to determine the amount of normal tissue of the subchondral bone plate, and consist of subchondral bone plate marking lines delineating a regular radioopaque linear structure within the position of the original joint space; and a subchondral bone plate reference line in the centre of the rectangular square as defined hereinbefore, having a length corresponding to twice the height of said rectangular square and a width corresponding to the width of the subchondral bone plate line markings; and wherein the proportion of the subchondral bone plate marking lines within the subchondral bone plate reference line is indicative for the amount of normal tissue of the subchondral bone. Accordingly, in a further aspect, the system comprises computational means to calculate the amount of normal tissue of the subchondral bone plate is represented as;

$$A_{bp}(\%) = 100 \times \frac{(\#Pix_{sblm})}{\#Pix_{sbrl}}$$

wherein; $A_{bp}$=the amount of normal subchondral bone plate
$\#Pix_{sblm}$=the amount of pixels of the subchondral bone plate line marking, wherein said pixels are either set using a user guided electronic ruler, using automatic pattern recognition techniques and/or edge detection techniques, or using a predefined reference pixel value for the subchondral bone plate structure.
$\#Pix_{sbrl}$ the total number of pixels found within the subchondral bone plate reference line, wherein the length of said line corresponds to twice the twice the height of said rectangle, and wherein the width of said line corresponds to the width of the subchondral bone plate line marking A third set of landmarks selected on the radiographs using the input means of the aforementioned system, allows to determine the amount of a normal joint space and consist of the subchondral bone plate marking lines as defined hereinbefore; the translucent area bordered with said subchondral bone plate marking lines; and a joint space reference plane in the centre of the rectangular square provided herein, having a length corresponding to the height of said rectangular and a width corresponding to the width of the translucent area bordered with said subchondral bone plate marking lines; and wherein the proportion of the radiotranslucent area bordered with 2 regular radioopaque linear structures within said joint space reference plane is indicative for the amount of a normal joint space. Accordingly, in a further aspect, the system comprises computational means to calculate the amount of normal joint space is represented as;

$$A_{js}(\%) = 100 \times \frac{(\#Pix_{tajs})}{\#Pix_{jsrl}}$$

wherein; $A_{js}$=the amount of normal joint space
- $\#Pix_{tajs}$=the amount of pixels of the translucent area bordered (flanked) by subchondral bone plate marking, either taken as a whole or as the number of pixels in a joint space line marking (supra)
- $\#Pix_{jsrl}$=the total number of pixels found within the joint space reference, wherein the reference is either a plane or a line in the centre of the rectangle square, having a length that corresponds to the height of said rectangle, and a width that equals either the width of the translucent area above or the width of the joint space line marking In a further aspect and as part of the measuring system, electronic programs are utilized, by which the radiographic images (such as DICOM or other related file forms) of the selected parts obtained in the ways outlined above are visualised. Said programs also may improve the visualization of the image. Program software provides a wide selection of measurement tools in electronic form (line, ruler, angles, circle, midline with various functional characteristics for adding right angles or parallel lines). Software tools are used to measure objects in the image, including number of pixels, pixel values and pixel locations of the desired imaged parts (normal bone, bone plate or joint space) and store said coordinates in mathematical form. Mathematical solutions according to the aforementioned formulae are subsequently applied to these collected data to determine the amount of normal tissue of the subchondral bone, the amount of normal tissue of the subchondral bone plate, and the amount of a normal joint space.

Thus in a further aspect, the system further comprises software, compatible with industry standards (currently DICOM3, HLA 7), embodying a series of electronic tools (line, ruler, angles, circle, midline with various functional characteristics for adding right angles or parallel lines) used for the identification and localisation of the bone and joint landmarks.

Software algorithms that compute these acquired data to provide the amount of normal tissue of the subchondral bone ($A_{sb}$), the amount of normal tissue of the subchondral bone plate ($A_{bp}$), and the amount of a normal joint space ($A_{js}$) are also within the admet of the system according to the present invention. In a particular embodiment, said software algorithm gives an overall numerical score or total score per interphalangeal finger joint; i.e. Total Score=$A_{sb}$+$A_{bp}$+$A_{js}$.

Eventually, the outgrowth of bone at the margins of a remodeling IP joint defined as the width of the joint can be taken into consideration in the scoring system as the proportion of joint width of the distal and proximal IP joints, relative to the diameter of the diaphysis of the flanking intermediate phalange (see FIG. 6).

The generation of a widened pseudo-joint space with irregular margins is the consequence of both the destruction of the subchondral plate and the osteolytic events in the subchondral bone area. These parameters are already taken into account in the amount of normal tissue of the subchondral bone and in the amount of normal tissue of the subchondral bone plate. Therefore, this variable was not considered in the scoring system of the present invention.

In an embodiment of the invention the series of the at least two consecutive radiographs can be taken within a time interval of at least six months. More in particular said time interval can be six, seven, eight, nine, ten, eleven, twelve or more months.

In another embodiment of the invention the method is performed on an interphalangeal finger joint. In particular the interphalangeal finger joint is a distal and/or a proximal interphalangeal joint. More in particular the interphalangeal finger joint is a proximal interphalangeal joint. The method can be performed on one, two, three, four or five distal or proximal interphalangeal joints. The method can also independently be performed on one, two, three, four or five distal and one, two, three, four or five proximal interphalangeal joints.

In yet another embodiment of the invention the variables can be indicated manually or automatically as a surface or a line.

From the radiographic data obtained in the above mentioned patients with erosive IP OA, 90 radiographs of 30 IP joints that initially were in the previously described "E" phase and showed further destruction as well as repair during follow-up, were used for testing the new and original scoring system of the present invention.

Thus, the present invention provides a method to monitor disease progression in a subject with erosive osteoarthritis of the interphalangeal finger joints characterized by determining the following three variables
- the amount of normal tissue of the subchondral bone,
- the amount of normal tissue of the subchondral bone plate, and
- the presence of a normal joint space on a series of at least two consecutive radiographs of the same interphalangeal finger joint of said subject.

Grading the presence/absence of lesions in the 3 well-defined tissue compartments: the subchondral bone, the subchondral bone plate and the synovial joint space can be performed on a stepwise incremental scale. Summation of the 3 subdomain scores then allows to generate an overall score for an IP finger joint in whichever phase of the disease.

Hence, in an embodiment of the method of the invention, the variables can be translated in numerical scores.

In another embodiment the numerical scores of the first three variables (the amount of normal tissue of the subchondral bone, the amount of normal tissue of the subchondral bone plate and the presence of a normal joint space) can be recorded on an incremental Lickert scale ranging from 0 to 100.

In another embodiment of the present invention, grading the presence/absence of lesions in the 3 well-defined tissue compartments, can be done by determining the proportion of normal/abnormal bone architecture within a defined rectangular square, on Visual Analogue Scales (VAS), or by making use of graphics editing computer programs. The defined rectangular square, characterized by having a height equal to the width of the joint space, is positioned such that the joint space is located in the centre of this square (see FIG. 13B). Areas, within the defined rectangular square, where osteolytic activity and remodeling caused disarrangement of the trabecular pattern, or where a complete loss of the trabecular structure had occurred can subsequently be marked on the radiographs (see FIG. 13C). Next, the percentage amount of normal/pathological looking bone in this area is quantified on VAS or by making use of graphics editing computer programs. In said latter, areas defining normal or pathological bone can for example be dyed in two different grayscales (see FIG. 13D), after which computed proportions of pixels stained with these different colors can be determined to analyze the proportion of normal/abnormal bone architecture.

In a preferred embodiment, the sum of the numerical scores, determined by any of the methods described above (incremental scale, VAS or computed) can give an overall numerical score or total score per interphalangeal finger joint of said subject.

Based on the aforementioned definitions of the three variables, the Total Score accordingly corresponds to;

$$\text{Total Score} = A_{sb} + A_{bp} + A_{js}$$

A decrease in the overall numerical score or 'Total Score' will be indicative for destruction of said interphalangeal finger joint and an increase in the overall numerical score or 'Total Score' will be indicative for remodeling/repair of said interphalangeal finger joint.

Thus in an embodiment of the invention, the method monitors disease progression in a continuous way. More in particular the method monitors disease progression in subjects with erosive osteoarthritis of the interphalangeal finger joints in a continuous way. Said disease progression can be natural or drug-modified. The method can calculate natural or drug-modified disease progression. Said calculated drug-modified disease progression can be used to identify or evaluate the effects of said drug. Hence the method can be used to identify or evaluate the effects of a drug. Said drug can have anticatabolic or repair promoting effects.

In a last embodiment the method of the invention is used to determine a method of treatment for the subject with erosive osteoarthritis of the interphalangeal finger joints, e.g. the results obtained with the method of the invention can determine the kind of treatment and when treatment should be started, adapted, changed or finished.

EXPERIMENTAL PART

Example 1

The Ghent University Scoring System (GUSS™)

Material and Methods

Patients and interphalangeal finger joints selection. Thirty interphalangeal (IP) finger joints showing erosive disease were selected from 18 patients with erosive hand osteoarthritis (OA) and in whom other rheumatic conditions were excluded. These subjects had participated in a one-year randomized, placebo-controlled, double-blind study (EudraCT number 2006-000925-71) to evaluate the potential of a Tumour Necrosis Factor (TNF) □-blocking monoclonal antibody to slow down destruction and to promote remodeling of the affected finger joints. Accordingly, the condition to be included in this therapeutic trial was the presence of one or more IP joints presenting the destructive "J" or "E" phases described previously (Verbruggen et al., 2002). Apart from the 18 selected "E" phase target joints, the radiographs presented 1 IP finger joint in the "S" (non-erosive OA) phase, 9 IP joints in the "J" phase (joints in which the joint space had disappeared) and 2 "R" (fully remodelled) IP finger joints.

Development of reference atlas. Three atlases of photographs were developed from the posteroanterior radiographs of the hands obtained during the study. The pictures enable the readers to score the amount of normal tissue of the subchondral bone (FIG. 3), the amount of normal tissue of the subchondral bone plate (FIG. 4), the presence of a normal joint space (FIG. 5) and the width of the joint (FIG. 6).

Radiographs, selection and blinding. Posteroanterior radiographs of the joints were obtained at baseline and after 6 and 12 months. In total 90 images were as such obtained and subsequently numbered randomly from 1-90.

Score of erosive changes. Three variables were selected to grade the severity of the radiographic changes: the proportions of the subchondral bone showing osteolytic areas, the relative amount of the subchondral bone plate resorbed by osteoclastic activity, and the disappearance of the normal joint space, either by an entire loss of the articular cartilage or by a complete destruction of the subchondral bone plate and the appearance of a pseudo joint. The pictures were scrambled and presented to 2 experienced readers (R1+R2) that performed the scorings separately. They were unaware of the patient's identity, drug assignment, time sequence of the radiographs and each other's measurements. Before starting the readings, they underwent two training sessions together on the same radiographs to identify discrepancies and inconsistencies with respect to the scoring method and to try to reduce their disagreement.

Score of remodelling in "E" and "E/R" joints. Some of the "E" IP joints showed apparent signs of remodelling during follow-up. Changes typical of tissue repair in these IP joints ("E/R" joints) were defined as disappearance of the osteolytic areas in the subchondral bone and the proportions of ordinary subchondral bone area thus recovered, in addition to a reconstruction of the subchondral bone plate. The latter went along with the reappearance of a distinct joint space. Remodelling was thus scored in the same three areas retained to grade erosive changes.

Computation of the changes in IP joints in "J", "E" and "E/R" phases. The 90 images were read in single order to evaluate the extent of the pathological changes in the three selected areas of the IP finger joint. The proportional amounts of normal tissue still present during a "J" or "E" phase or that reappeared during remodelling ("E/R" and "R" phase) were recorded on a 10-point incremental Likert scale ranging from 0 to 100. The sum of the three separate scorings constitutes the total IP joint score. Equal weight was attributed to each of the subdomains. In addition, a longitudinal analysis was done after arranging the results of the readings in the correct sequence.

Statistics. Descriptive clinical and radiographic data were recorded at baseline for the 18 patients selected. Data were summarized using the mean for normally distributed, continuous variables, and the median (minimum–maximum) for non-normally distributed variables. Cross sectional radiographic data are presented for each reader (R1 and R2) and the mean for both readers for the 3 timepoints. Longitudinal data are presented as mean change score for both readers. Intra- and interreader reliability was assessed using Intraclass Coefficient of Correlation (ICC). Estimates of the 95% confidence interval (95% C.I.) were calculated. Reproducibility of the categorical scoring system was evaluated by the percentage of absolute agreement between readers and readings and by unweighted Kappa (□) statistics. Responsiveness, the degree of progression of radiological joint damage above the measurement error is best determined by the smallest detectable change (SDC=±1.96×SD□(change-scores between raters)/(□k×□2), where 'k' represents the number of readings or raters used for the actual analyses of a trial. Calculating these cut-off values allowed us to express the results in simple categories such as the number of patients who improved, worsened, or remained stable. Sensitivity to change of the scoring system is estimated on the basis of differences between the 12 months timepoint and the baseline, using the standardized response mean (SRM=mean change/SD of change). All statistical analyses were performed using the statistical software package SPSS 15.0.

Results

Study Materials

18 Patients, 15 females and 3 males of Caucasian origin, with erosive osteoarthritis of the distal IP and/or proximal IP finger joints were selected. The mean age at baseline was 60.8 years (SD: 8.7) and the disease duration was 11.3 years (range: 1.1-40.9). All patients were negative for rheumatoid or antinuclear factors. None of them carried the HLA-B27 antigen or did present any sign of a spondylarthropathy-associated arthritis. On average 12.5 of 16 IP joint showed osteoarthritic changes, with respectively 5, 0.5, 3 and 4 joints in "S", "J", "E" and "R" phase. The IP joints of the thumb were excluded.

Cross-sectional Analysis

The pictures obtained from the 30 IP joints at 3 time points totaling 90 photographs, were scrambled and presented to 2 experienced readers (R1 and R2) that performed the scorings separately. They were unaware of the patient's identity, drug assignment, time sequence of the radiographs and each other's measurements. Before starting the readings, they underwent two training sessions together on the same radiographs to identify discrepancies and inconsistencies with respect to the scoring method and to try to reduce their disagreement.

Aside from the one "E" joint that allowed the patients to be included in the study, most patients showed some of their IP joints already in the "R" phase on admission in the study. The morbidity of the changes in these "E" and "R" joints varied considerably. In addition, destructive events and remodeling in these IP joints showed considerable overlap. The series of radiographs in FIG. 2A illustrate this statement. The readers were asked to define the anatomical phase of the affected joints ("E" or "R") according to the previously mentioned method. Later on, this exercise enabled the scores of the amount of normal tissue of the subchondral bone and of the subchondral bone plate and those of the presence of a normal joint space for "E" and "R" IP joints to be compared.

Figure 7:
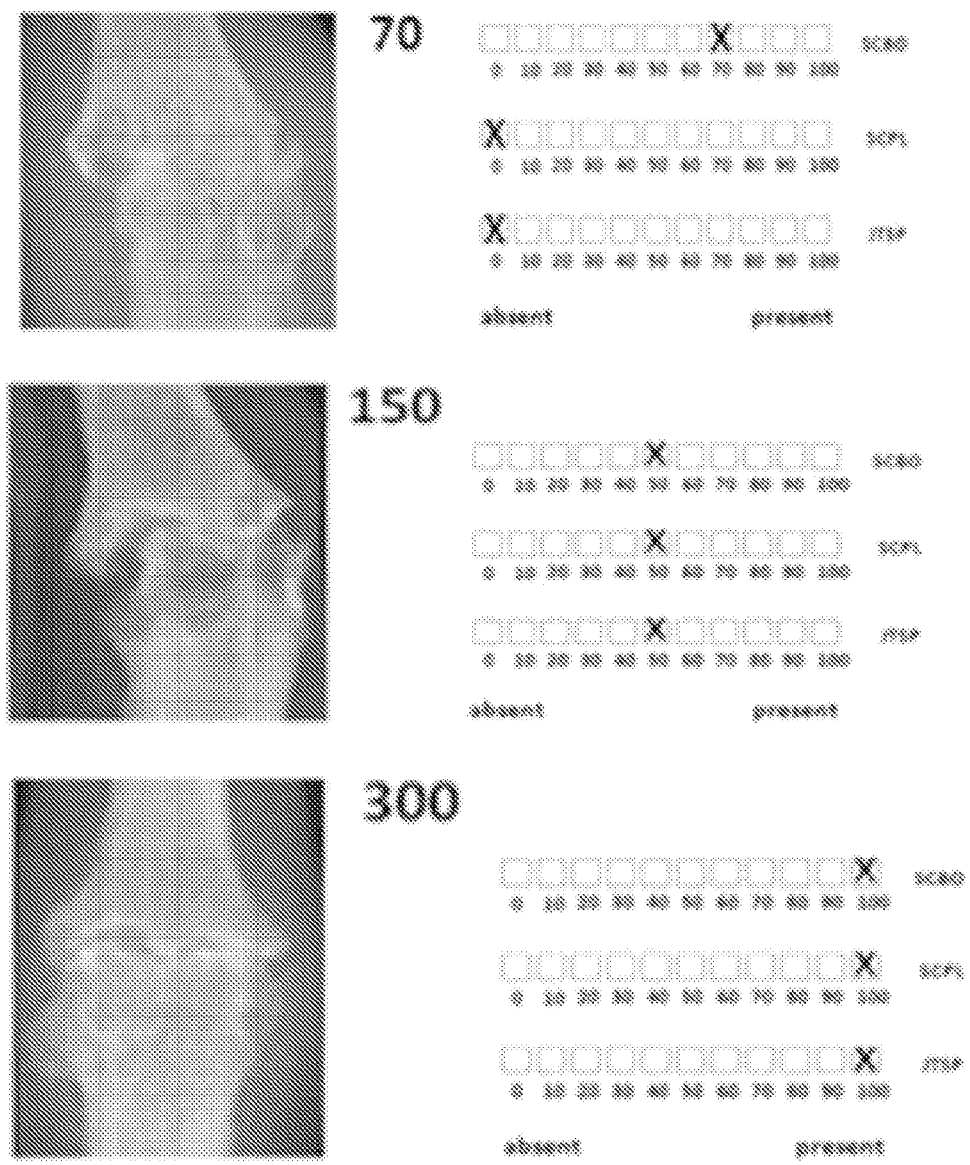
FIG. 7: Evaluation of the amount of normal tissue of the subchondral bone (SCBO), the amount of normal tissue of the subchondral bone plate (SCPL) and the presence of a normal joint space (JTSP). The changes in these 3 variables were recorded on a 10-point incremental Lickert scale ranging from 0 to 100. Total scores are given for each of the 3 IP joints.
Figure 8:
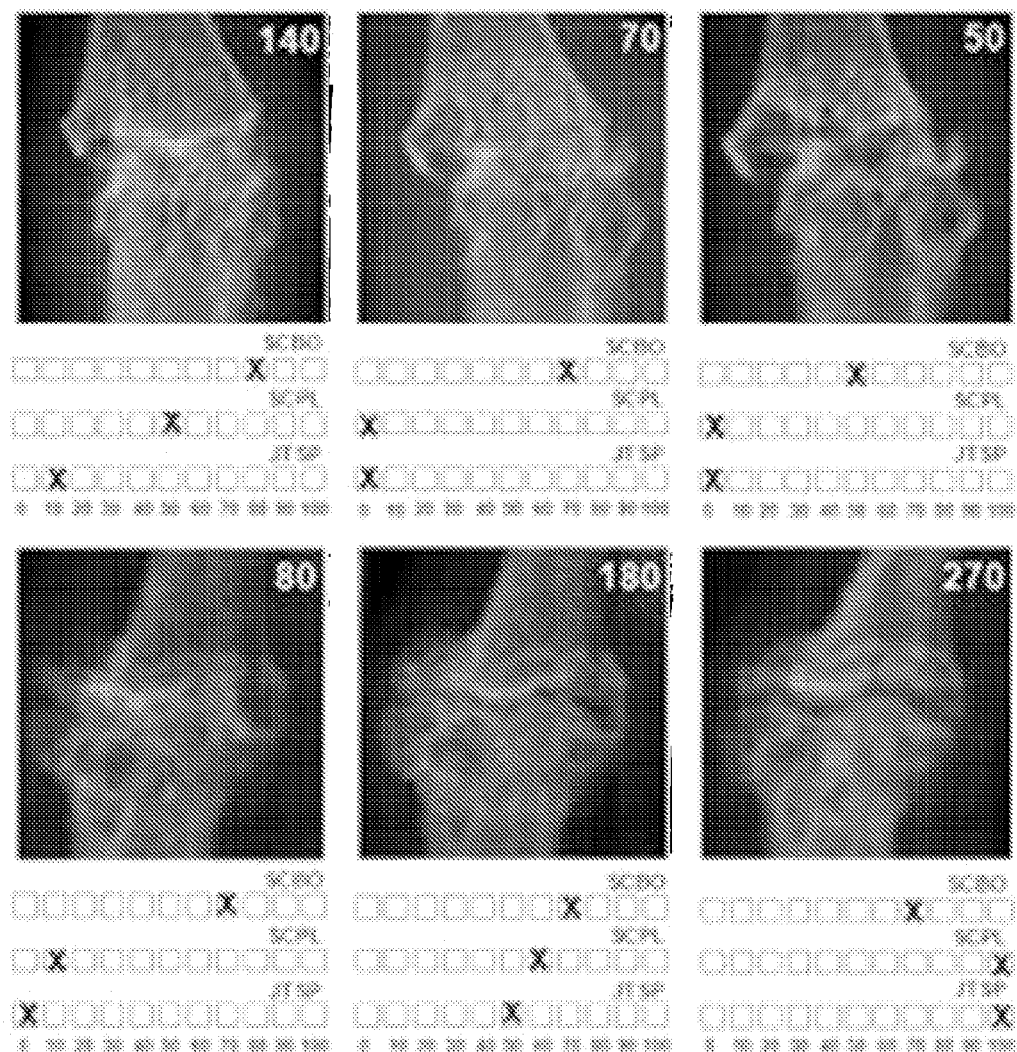
FIG. 8: Evaluation of the amount of normal tissue of the subchondral bone (SCBO), the amount of normal tissue of the subchondral bone plate (SCPL) and the presence of a normal joint space (JTSP). The changes in these 3 variables were recorded on a 10-point incremental Lickert scale ranging from 0 to 100. Total scores are given for each of the 3 IP joints. The analysis was done on 2 series of IP joints radiographed at start and after 6 and 12 months of follow-up. The readers knew the order in which the radiograms were obtained. Top series: IP joint going through "E" phase. Bottom series: remodeling IP joint.

Thus after the scoring of the anatomical phase, the series of 90 scrambled pictures from the 30 IP joints at 3 time points were used by the readers to evaluate the amount of normal tissue of the subchondral bone, the amount of normal tissue of the subchondral bone plate and the presence of a normal joint space. Total scores on a 10-point incremental Lickert scale ranging from 0 to 100 were given for each of the 3 IP joints (FIG. 7). The sum of the three separate scorings constituted the total IP joint score. Equal weight was attributed to each of the subdomains. In addition, the same analysis was done on the 30 IP joints at 3 time points presented in the correct sequence. This exercise was done to judge the amount of bias produced resulting from the readers' knowledge of the order in which the radiograms were obtained (FIG. 8). Mean scores per subdomain and the total score for each reader and reading are shown in table 1.

TABLE 1

Cross-sectional analysis (N = 90): Mean scores per subdomain and for the total score per reader and per reading of the radiographs read in single order and reliability analysis by ICC (95% CI)

| Var. | RD | Mean (SD) Reading 1 | Mean (SD) Reading 2 | Intra-reader reliability ICC (95% CI) Reading 1 – Reading 2 | RD | Inter-reader reliability ICC (95% CI) Reading 1 – Reading 1 |
|---|---|---|---|---|---|---|
| SCBO | 1 | 60.2 (22.5) | 67.9 (21.4) | 0.79 (0.70-0.82) | 1-2 | 0.74 (0.62-0.82) |
|  | 2 | 66.3 (21.4) | 72.2 (20.0) | 0.85 (0.78-0.90) |  |  |
| SCPL | 1 | 44.1 (27.8) | 45.3 (27.3) | 0.85 (0.78-0.90) | 1-2 | 0.82 (0.74-0.88) |
|  | 2 | 50.6 (28.9) | 52.3 (27.9) | 0.88 (0.82-0.92) |  |  |
| JTSP | 1 | 37.6 (32.0) | 32.7 (31.1) | 0.84 (0.76-0.89) | 1-2 | 0.79 (0.70-0.86) |
|  | 2 | 35.4 (31.7) | 36.6 (31.2) | 0.94 (0.91-0.96) |  |  |
| Total score | 1 | 141.9 (68.6) | 145.9 (64.1) | 0.88 (0.82-0.92) | 1-2 | 0.84 (0.76-0.89) |
|  | 2 | 152.3 (67.4) | 160.9 (64.8) | 0.93 (0.90-0.96) |  |  |

SD: standard deviation; ICC: intraclass coefficient of correlation; CI: confidence interval; SCBO: subchondral bone; SCPL: subchondral plate; JTSP: joint space; RD: reader Cross-sectional intra- and interobserver reproducibility of scorings was calculated on the data from the readings of the radiographs in single order. ICC values and their 95% CI were high for both readers, ranging from 0.79 to 0.94. The lowest ICC was obtained by both readers for the subdomain subchondral bone. ICC (95% CI) for each reader are shown in table 1. Interobserver ICC values are 0.74 for the subchondral bone, 0.82 for the subchondral plate, 0.79 for the joint space and 0.84 for the total score, exhibiting a good reproducibility for all scores.

After further training of the readers, another reading was performed in which the intra- and inter-reader reliability was within the range of the data as shown in table 1.

Longitudinal Analysis

Interobserver and intraobserver reproducibility. ICC values (95% CI) between repeated scorings of changes between the 12 months timepoint and baseline, and the 6 months timepoint and baseline radiographs are given in table 2 for each reader and between readers. ICC values are excellent for reader 2 on all variables ranging from 0.97 to 0.99. Reader 1 scores well for subchondral plate, joint space and the total score with ICC of 0.91, 0.88, and 0.85 for change between the baseline and the 6 months timepoint, respectively and 0.91, 0.94, and 0.96 for change between baseline and the 12 months timepoint, respectively. ICC values for subchondral bone score moderate for reader 1 (table 2). Interreader ICC scores rate very good for subchondral plate, joint space and total score and good for subchondral bone over a time interval of 12 months.

Changes in Score Over Time.

Figure 9:
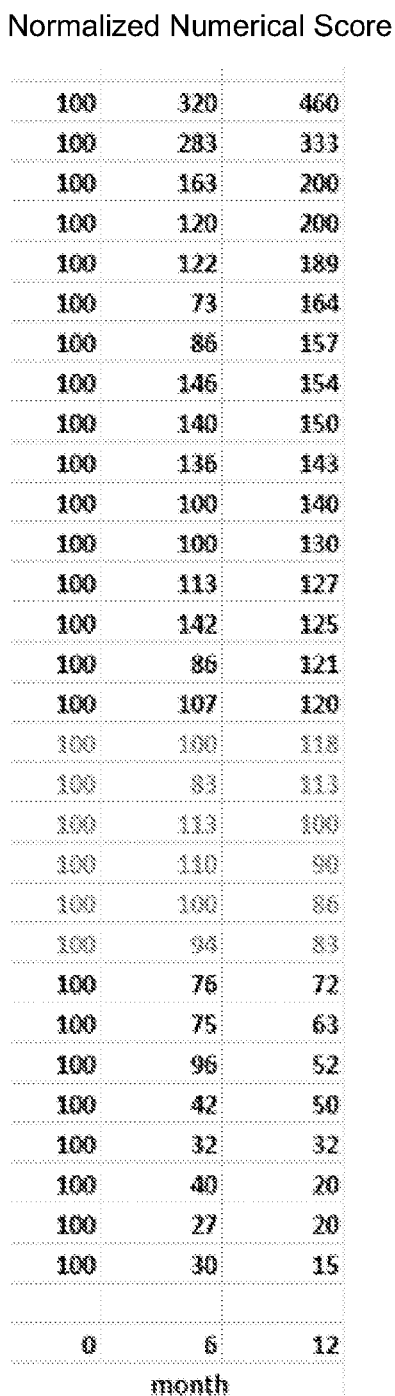
FIG. 9: Normalized scores over 1 year in the 30 IP joint population, wherein the cumulative score at day 0 is set at 100%. Less than 20% percentage change in normalized score (dotted line on the graph) is considered unchanged.
Figure 9:
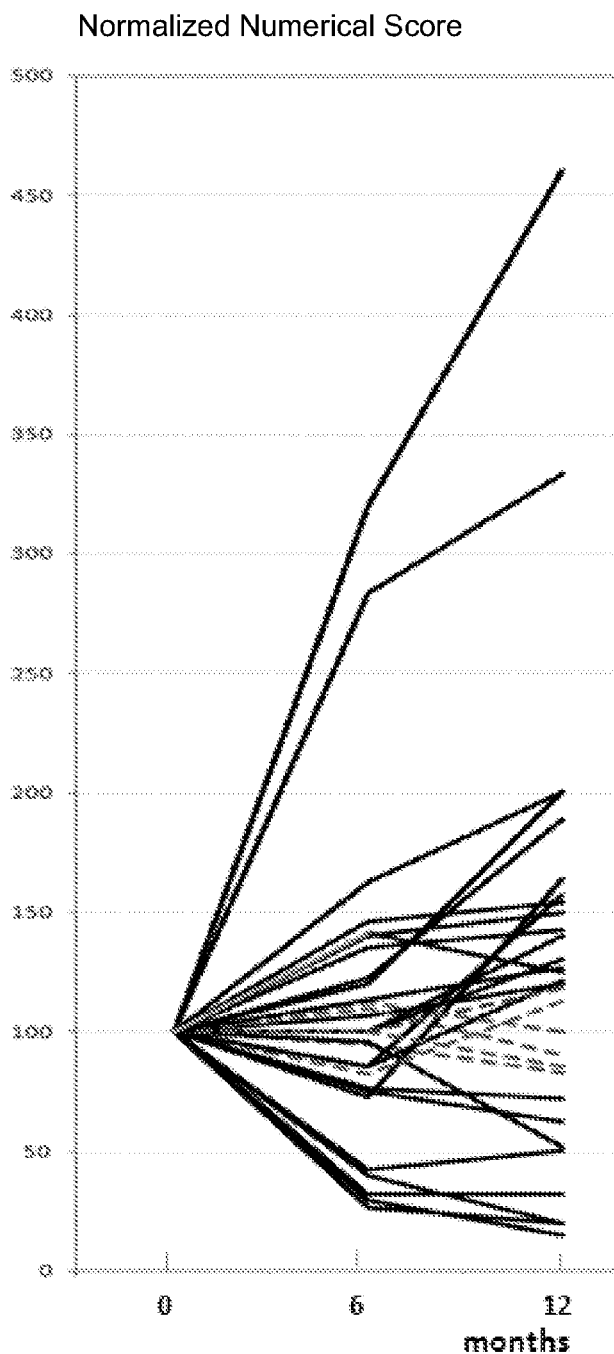

Normalized scores over 1 year in the 30 IP joint population, wherein the cumulative score at day 0 is set at 100% are represented in FIG. 9. These data demonstrate the strength of the present methodology in determining a change within a short period of time like for example 6 months.

TABLE 2

Longitudinal analysis (N = 90): Mean changes in scorings after 6 and 12 months of follow-up, reliability analysis by intraclass coefficient of correlation, and responsiveness by the smallest detectable change.

| | | Intra-reader reliability | | | Inter-reader reliability | | Responsiveness M 0-M 12 | | M 0-M 6 | |
|---|---|---|---|---|---|---|---|---|---|---|
| Var. | RD | □M 0-M 6 ICC (95% CI) | □M 0-M 12 ICC (95% CI) | RD | □M 0-M 6 ICC (95% CI) | □M 0-M 12 ICC (95% CI) | Mean □ between readers (SD) | SDC | Mean □ between readers (SD) | SDC |
| SCBO | 1 | 0.73 (0.51-0.86) | 0.75 (0.53-0.87) | 1-2 | 0.63 (0.36-0.81) | 0.86 (0.72-0.93) | 9.3 (12.9) | 17.8 | 14.0 (16.9) | 23.5 |
| | 2 | 0.99 (0.97-0.99) | 0.99 (0.99-0.99) | | | | | | | |
| SCPL | 1 | 0.91 (0.83-0.96) | 0.91 (0.83-0.95) | 1-2 | 0.87 (0.74-0.93) | 0.90 (0.81-0.95) | 10.3 (11.9) | 16.5 | 11.3 (15.5) | 21.5 |
| | 2 | 0.99 (0.99-0.99) | 0.99 (0.99-0.99) | | | | | | | |
| JTSP | 1 | 0.88 (0.76-0.94) | 0.94 (0.88-0.97) | 1-2 | 0.83 (0.68-0.92) | 0.91 (0.81-0.96) | 13.7 (15.4) | 21.4 | 17.3 (21.0) | 29.1 |
| | 2 | 0.99 (0.99-0.99) | 0.99 (0.99-0.99) | | | | | | | |
| Total score | 1 | 0.85 (0.71-0.93) | 0.96 (0.91-0.98) | 1-2 | 0.86 (0.73-0.93) | 0.93 (0.86-0.97) | 26.0 (25.9) | 36.0 | 32.7 (34.3) | 47.6 |
| | 2 | 0.99 (0.99-0.99) | 0.99 (0.99-1.00) | | | | | | | |

SCBO: subchondral bone; SCPL: subchondral plate; JTSP: joint space; RD: reader; ICC = intraclass coefficient of correlation; M 0: baseline; M 6: month 6; M 12: month 12; □: change in score; Smallest detectable change (SDC) = ±1.96 × SD □ (change score)/(□2 × □k); k = 1, if not using average scores.

Responsiveness.

Figure 10:
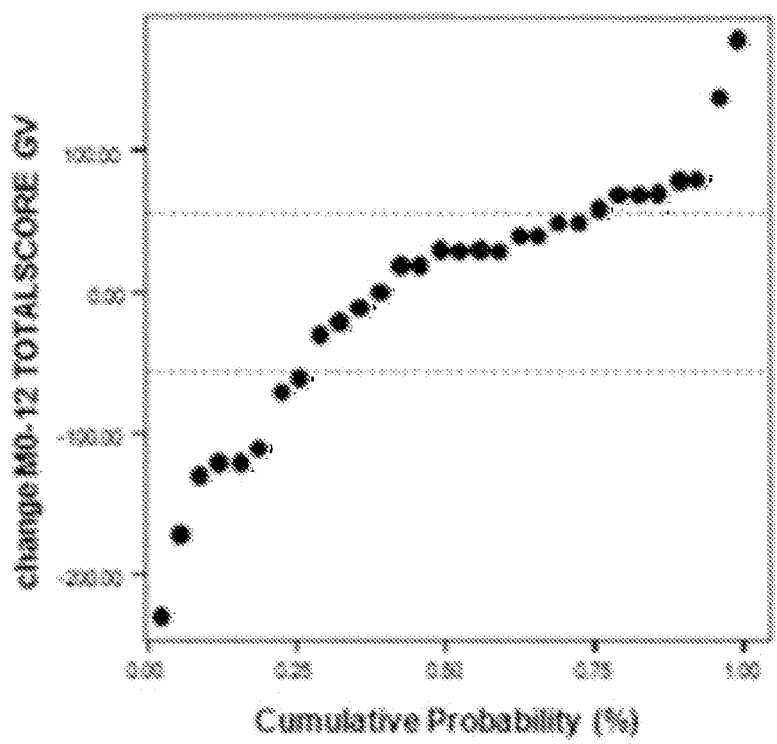
FIG. 10: Cumulative probability plot of one year radiographic progression. Cut-off was defined by the smallest detectable difference (SDC=36.0)–dotted lines.

The mean differences with the standard deviation (M□±1 SD) and calculated SDC are shown in table 2. SDC for the total score over 6 and 12 months equals 47.6 and 36.0 units, meaning that a change obtained over 6 months of 50 units or more, and over 12 months of 40 or more on the total score can be interpreted as a real change. Smaller changes should be interpreted as measurement error or 'reproducibility noise'. Defining upper and lower cut-off levels of 'real' change (i.e., -SDC, +SDC) allowed us to detect radiographic progression and divide the set of IP finger joints into 'progressors' (which means in this case remodelling or progression to more erosive OA) and IP joints that remain stable. The cumulative probability plot in FIG. 10 shows that a number of IP joints (n=12) showed significant remodelling over 12 months (change of total score>SDC, in this case □ 36). Similarly, 9 IP joints progressed to more erosive disease. Nine joints remained stable. The new scoring system, GUSS™ (Ghent University Scoring system), allowed classifying 70.0% of joints as 'progressors'. In the same way, an absolute change in total score exceeding a SDC of 47.6 between baseline and the 6 months timepoint in 18 IP finger joints allowed 60% of these joints to be classified 'progressors'.

Sensitivity to Change.

The standardized response means (SRM=mean change/standard deviation of change) are rather low (table 3), ranging from 0.19 to 0.32 for reader 1 (SRM=0.21, 0.24, 0.32, and 0.19 respectively for subchondral bone, subchondral plate, joint space, and total score) and 0.19 to 0.47 for reader 2 (SRM=0.24, 0.19, 0.32, and 0.47 respectively for subchondral bone, subchondral plate, joints space, and total score). Joint space seems to be most responsive to both readers as well as the total score to reader 2.

TABLE 3

Smallest response mean calculated using the SRM obtained by both readers for all subdomains and the total score

| | SRM of RD1 | SRM of RD2 |
|---|---|---|
| SCBO | 0.25 | 0.09 |
| SCPL | 0.02 | 0.01 |

TABLE 3-continued

Smallest response mean calculated using the SRM obtained by both readers for all subdomains and the total score

| | SRM of RD1 | SRM of RD2 |
|---|---|---|
| JTSP | 0.16 | 0.13 |
| Total score | 0.01 | 0.09 |

SCBO: subchondral bone;
SCPL: subchondral plate;
JTSP: joint space;
SRM: standardized response mean;
RD: reader.

Mean Scores and SD-values of IP Finger Joints in Consecutive Anatomical Phases.

Figure 11:
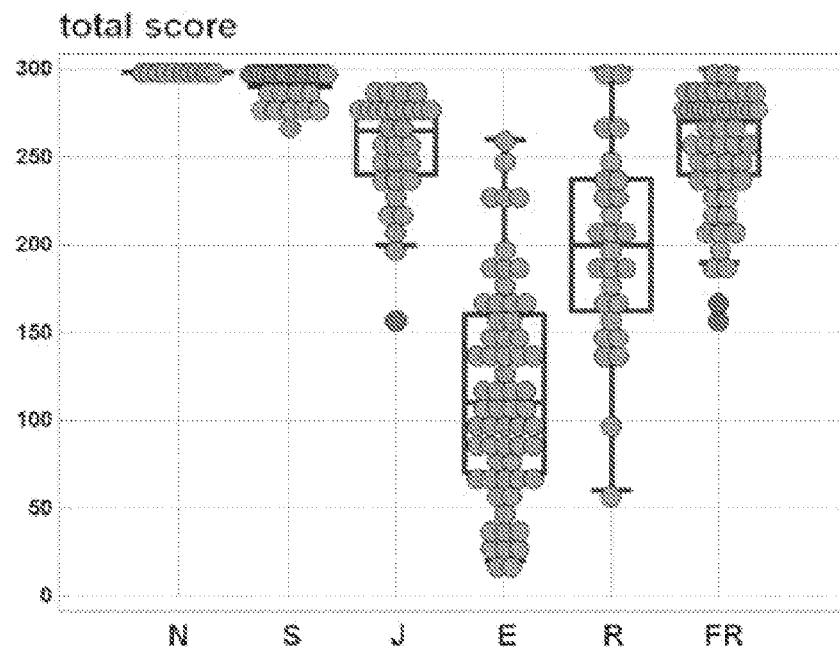
FIG. 11: Mean scores and SD-values of IP finger joints in consecutive anatomical phases. Individual total scores and Box & Whisker plots (median values lower and upper quartiles) are given for normal (N; n=10) IP joints, non-erosive OA joints (S; n=30), IP joints showing partial loss of the joint space (J; n=30), IP joints in the erosive phase (E; n=61), IP joints showing remodeling (R; n=27) and fully end-stage IP joints (FR; n=51). The "E" and "R" IP finger joints were from the series of 30 joints (90 radiographs) from the study population.

In addition to the scores obtained for the selected 90 "E" and "R" joints, scores were computed for 30 "S", 30 "J", and 51 randomly selected end-stage "R" IP joints. Of these series, the non-erosive "S" IP joints at most showed some subchondral cysts and sclerosis with an intact subchondral plate and some joint space narrowing and obtained a score which almost equaled that of the non-affected IP joints (median; lower-upper quartile: 300; 290-300). Normal "N" IP joints per se scored 300. Partial loss of the joint space in "J" IP joints caused a drop in the scores (median; lower-upper quartile: 265; 240-280). The pathological changes in the different compartments in "E" joints significantly reduced the total scores of these joints (median; lower-upper quartile: 110; 70-150). Remodeling of the tissues produced an increase of the respective scores (median; lower-upper quartile: 200; 165-235) (FIG. 11) and fully remodeled "R" IP joints in this study population attained a median total score of 270 with lower and upper quartiles of 240 and 280, respectively.

Example 2

Comparison of the Categorical Anatomical Phase Scoring System and the Optimized GUSS™ Model Successive pathological phases recognized in the course of IP finger joint OA allowed gross changes in the progression of this disease to be recorded over a 3-years period with the categorical anatomical phase scoring system (CAPSS). However, this analytical system based on changes in categorical variables did not allow discriminating between subtle changes in anatomical progression occurring in shorter time studies. Destruction and reconstruction of subchondral bone and bone plate, and of the synovial joint space of the affected IP joints has shown considerable variation in morbidity and occurred much more rapidly than previously recognized. To evaluate whether our newly developed GUSS™ model is able to identify more subtle changes in the IP finger joints and within a shorter period of time, we evaluated our IP finger joint cohort from example 1 with the CAPSS model and compared the results with the GUSS™ model.

Progression of selected IP joints through categorical anatomical phases. "S", "J", "E" or "R" phases were assigned to all images. The percentage of absolute agreement between the readers is 93.6% ($\square$ =0.92). The intrareader reliability for both readers is excellent with a percentage of absolute agreement of 95.9% ($\square$ =0.95) for reader 1 and 98.2% ($\square$ =0.98) for reader 2.

Disease progression over 6 months is detected in up to 18 (60.0%) out of the 30 target joints with the GUSS™ model (table 4). More erosive disease or obvious remodelling occurred in 11 (36.7%) and 7 (23.3%) out of these 18 IP finger joints. The previous CAPSS allowed 10 (33.3%) of these IP joints to be classified as progressors. Six and four IP joints, respectively, were recognized as more erosive or showed signs of repair. GUSS™ detected significantly more progression after 6 months (GUSS™ 18/30, CAPSS 10/30; McNemar's test p<0.008). No significant differences were observed between GUSS™ and CAPSS after 12 months (GUSS™ 21/30 and CAPSS 17/30; McNemar's test p=0.125). Progressive changes over a longer period i.e. 12 months allowed more IP joints to move into a subsequent anatomical phase, resulting in comparable scoring for both measuring models.

Using the CAPSS for the IP finger joint cohort from example 1, 17 out of 30 (56.7%) joints were defined as progressors from baseline to the 12 months timepoint (table 4): 8 of these showing further features of destruction and 9 of obvious repair in the selected areas of the joint. With the GUSS™ scoring system, however, significant disease progression had occurred in 21 out of 30 (70.0%) IP joints. More erosive disease or remodelling had occurred in 9 and 12 out of the target joints, respectively.

TABLE 4 comparison of the categorical anatomical phase scoring system (CAPSS) with the Ghent University Scoring System (GUSS ™).

| | 6 months | | | 12 months | | |
|---|---|---|---|---|---|---|
| | Progression | Erosive | Repair | Progression | Erosive | Repair |
| GUSS ™ | 18/30 (60.0%) | 11/30 (36.7%) | 7/30 (23.3%) | 21/30 (70.0%) | 9/30 (30.0%) | 12/30 (40.0%) |
| CAPSS | 10/30 (33.3%) | 6/30 (20%) | 4/30 (13.3%) | 17/30 (56.7%) | 8/30 (26.7%) | 9/30 (30.0%) |

Example 3

Alternative Read-out of the GUSS™ Scoring Model, by Making Use of VAS or Graphics Editing Programs Assessment of normality and pathology in 5 different proximal interphalangeal finger joints was determined by making use of VAS (Visual Analogue Scale) as well as graphics editing programs. Thereto, a rectangular square of which the height equals the width of the joint space, was positioned such that the joint space was located in the centre of this square. The width of the joint space is indicated in FIG. 12A. The rectangular area wherein the bone architecture was evaluated is represented in FIG. 12B.

A. Subchondral Bone Area

Figure 12:
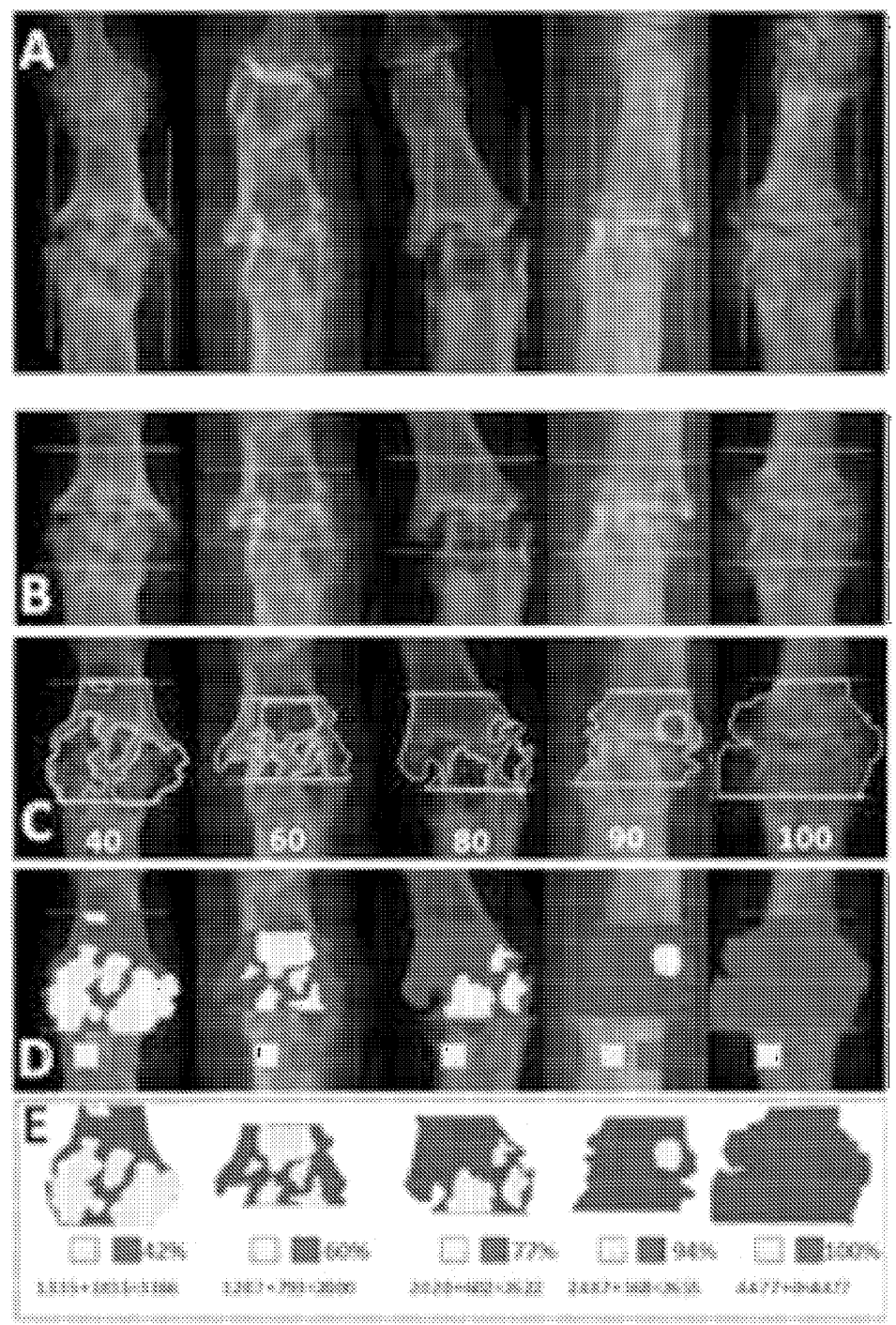
FIG. 12: Proportion of subchondral bone area with normal/abnormal looking bone architecture. A. Indication of the width of the joint space. B. Indication of the rectangular area wherein the bone architecture will be evaluated. C. Marking of the areas where osteolytic activity and remodeling caused a disarrangement of the trabecular pattern, or where a complete loss of the trabecular structure had occurred. Indicated scores were determined on VAS (Visual Analogue Scale). D. Areas defining normal or pathological bone were dyed in two different grayscales; 82 and 233 respectively on a scale up to 256 levels. E. Computed proportions of pixels stained with level 82 gray (normal bone) were assessed for the 5 consecutive finger joints.

Areas where osteolytic activity and remodelling caused a disarrangement of the trabecular pattern, or where a complete loss of the trabecular structure had occurred are marked in the predefined areas on the radiographs (FIG. 12C) and percentage amounts of normal/pathological looking bone in this area are quantified. Quantification done on VAS (Visual Analogue Scales), resulted in proportions of normal bone in the area of interest of 40, 60, 80, 90, and 100% for the 5 consecutive finger joints studied, respectively (FIG. 12C). Alternatively, areas defining normal or pathological bone were dyed in two different grayscales (FIG. 12 D). Using a graphics editing program the number of pixels with a defined grayscale level were computed. In classic digital graphics editing programs grayscales level up to 256 levels: from 0 to 255 for black to white, respectively. In FIG. 12 E, grayscale levels of 82 and 233 were used for normal and pathological areas, respectively. Computed proportions of pixels stained with level 82 gray (normal bone) were 42, 60, 77, 94 and 100% for the 5 consecutive finger joints studied.

B. Subchondral Plate

Figure 13:
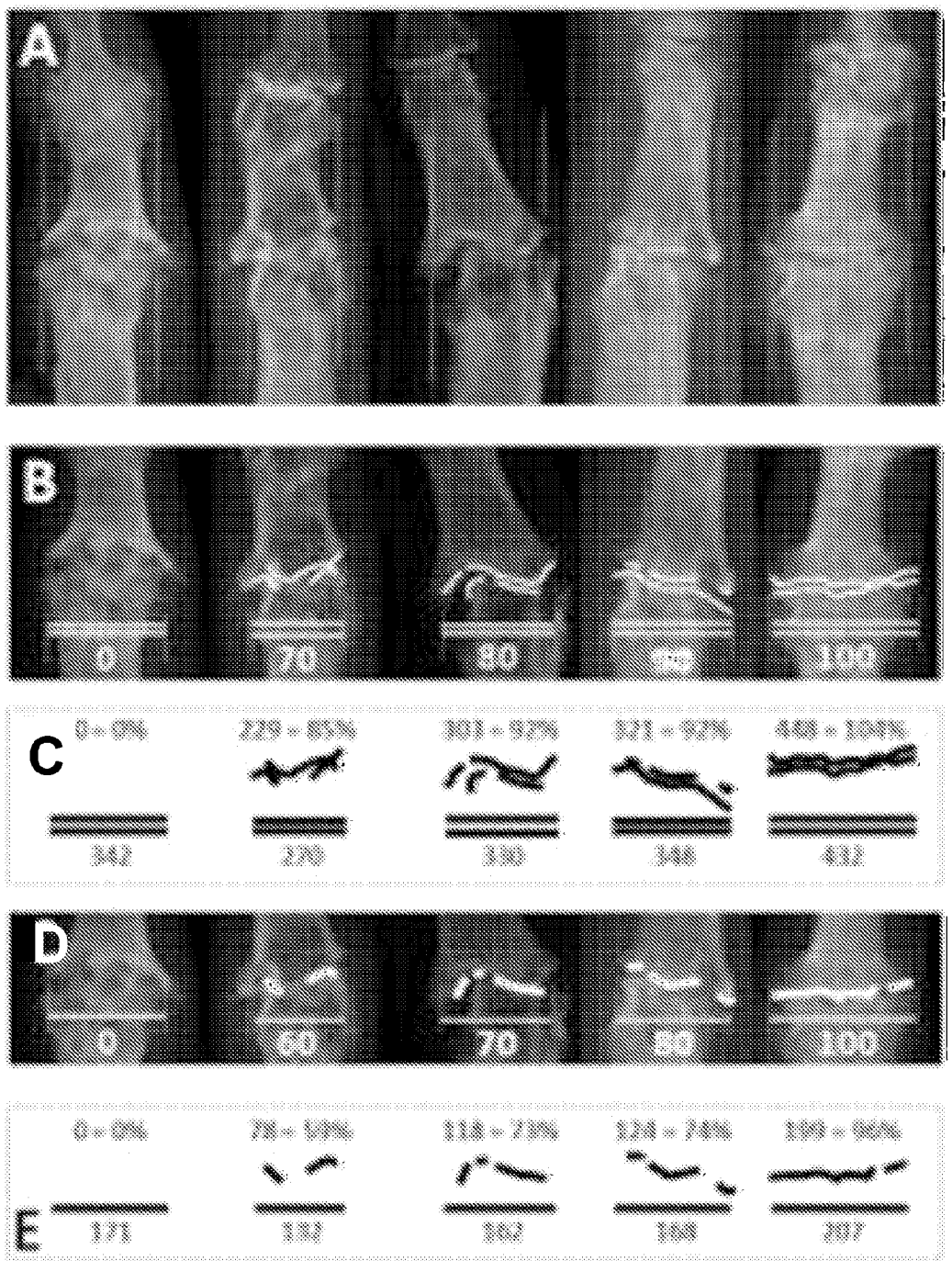
FIG. 13: Proportion of subchondral plate and synovial joint space with normal/abnormal looking bone architecture. A. Indication of the width of the joint space. B. Indication of the identifiable subchondral bone plate together with a double line representing the length of 2 subchondral bone plates bouding the synovial space. Indicated scores were determined on VAS (Visual Analogue Scale). C. Computed proportions of pixel in the line drawings representing the subchondral bone plate. D. Indication of the synovial joint space, recognized as a radiotranslucent area bordered with 2 subchondral plates, together with a single line representing the joint width. Indicated scores were determined on VAS (Visual Analogue Scale). E. Computed proportions of pixel in the line drawings representing the synovial joint space.

Assessment of normal/pathological subchondral plate is clarified in FIG. 13. Articular joint space width is indicated in FIG. 13A. Where the joint space is still identifiable, the subchondral bone plate is recognized as a regular linear bone margin flanking the joint space. Identifiable subchondral bone plates are marked in FIG. 13 B together with a double line representing the length of 2 subchondral bone plates bounding the synovial space. Percentage amounts of identified subchondral bone plate can be quantified on VA Scales. In FIG. 13B, the proportions of identified subchondral bone plate determined this way were 0, 70, 80, 90, and 100% for the 5 consecutive finger joints studied, respectively. In FIG. 13C these line markings are dyed in black. Using a graphics editing program the number of black pixels in the line drawings of both reference lines and subchondral bone markings are computed. The data obtained allow proportions of normal/pathological subchondral bone plate to be calculated. Computed proportions of pixels in the line drawings representing subchondral bone plate were 0, 85, 92, 92 and 104% for the 5 consecutive finger joints studied.

C. Synovial Joint Space

Assessment of synovial joint space is clarified in FIG. 14. Synovial joint space was recognized as a radiotranslucent area bordered with 2 subchondral plates (FIG. 13D). Identifiable synovial joint space is marked in FIG. 13D together with a single line representing the joint width. Percentage amounts of identified synovial joint space can be quantified on VA Scales. In FIG. 13D, the proportions of identified synovial joint space determined this way were 0, 60, 70, 80, and 100% for the 5 consecutive finger joints studied. In FIG. 13E these lines are dyed in black. Using a graphics editing program the number of black pixels in the line drawing of both reference joint width lines and synovial joint space markings are counted and these counts allow proportions of remaining synovial joint space to be calculated. Computed proportions of pixels in the line drawings representing synovial joint space were 0, 59, 73, 74 and 96% for the 5 consecutive finger joints studied.

REFERENCES

BÖTTCHER J, PFEIL A, ROSHOLM A, PETROVICH A, SEIDL B E, MALICH A, SCHAFER M L, KRAMER A, MENTZEL H J, LEHMAN G, HEIN G, KAISER W A.

Digital X-ray radiogrammetry combined with semiautomated analysis of joint space widths as a new diagnostic approach in rheumatoid arthritis. Arthritis Rheum 2005; 52, 2850-2859.

BUCKLAND-WRIGHT C, MACFARLANE D, LYNCH J. Quantitative microfocal radiographic assessment of disease and progression in osteoarthritis of the hand. J Rheumatol Suppl 1991; 27:40-41.

BUCKLAND-WRIGHT C. Subchondral bone changes in hand and knee osteoarthritis detected by radiography. Osteoarthritis Cartilage 2004; 12 Suppl A: S10-S19.

FINCKH A, DE PABLO P, KATZ J N, NEUMANN G, LU Y, WOLFE F, DURYEA J. Performance of an automated computer-based scoring method to assess joint space narrowing in rheumatoid arthritis. Arthritis Rheum 2006; 54, 1444-1450.

RAVAUD P, GIRAUDEAU B, AULELEY G R, EDOUARD-NOEL R, DOUGADOS M, CHASTANG C. Assessing smallest detectable change over time in continuous structural outcome measures: application to radiological change in knee osteoarthritis. J Clin Epidemiol 1999; 52, 1225-30.

SHARP J T, GARDNER J C, BENNETT E M. Computer-based methods for measuring joint space and estimating erosion volume in the finger and wrist joints of patients with rheumatoid arthritis. Arthritis Rheum 2000; 43, 1378-1386.

PATEL N, BUCKLAND-WRIGHT C. Advancement in the zone of calcified cartilage in osteoarthritic hands of patients detected by high definition macroradiography. Osteoarthritis Cartilage 1999; 7: 520-525.

VAN 'T KLOOSTER R, HENDRIKS E A, KLOPPRN-BURG M, REIBER J H, STOEL B C. Automatic quantification of osteoarthrtis in hand radiographs: validation of a new method to measure joint space width. Osteoarthritis Cartilage 2008; 16: 18-25 [Epub 2007 Jul. 16].

VERBRUGGEN G, VEYS E M. Numerical scoring systems for the anatomic evolution of osteoarthritis of the finger joints. Arthritis Rheum 1996; 39, 308-320.

VERBRUGGEN G, GOEMAERE S, VEYS E M. Chondroitin sulfate: S/DMOAD (structure/disease modifying anti-osteoarthritis drug) in the treatment of finger joint OA. Osteoarthritis Cartilage 1998; 6 Suppl A: 37-38.

VERBRUGGEN G, GOEMAERE S, VEYS E M. Systems to assess the progression of finger joint osteoarthritis and the effects of disease modifying osteoarthritis drugs. Clin Rheumatol 2002; 21, 231-43.

ZHANG W, DOHERTY M, LEEB B, ALEKSEEVA L, ARDEN N, BIJLSMA J, DINCER F, DIEDZIC K, HAUSELMANN H J, KAKLAMANIS P, LOHMANDER S, MAHEU E, MARTIN-MOLA E, PAVELKA K, PUNZI L, REITER S, SMOLEN J, VERBRUGGEN G, WATT I, ZIMMERMANN-GORSKA I. EULAR evidence based recommendations for the diagnosis of hand osteoarthritis-report of a task force of the EULAR Standing Committee for International Clinical Studies Including Therapeutics (ESCISIT). Ann Rheum Dis. 2008 Feb. 4. [Epub ahead of print]

What is claimed is:

1. A measuring device for analyzing a radiograph of an interphalangeal finger joint to obtain a numerical scoring for the grade of destruction or the grade of remodeling and repair of the interphalangeal finger joint, said device having input means to select landmarks on said radiograph and means for computing on the basis of the received landmarks;
the amount of normal tissue of the subchondral bone,
the amount of normal tissue of the subchondral bone plate, and
the amount of a normal joint space
on a series of at least two consecutive radiographs of the same interphalangeal finger joint of said subject; characterized in that;
the landmark to determine the amount of normal tissue of the subchondral bone consists of a rectangular square of which the height equals the width of the joint space, and wherein the joint space is positioned in the centre of this square;
the landmark to determine the amount of normal tissue of the subchondral plate consist of subchondral bone plate marking lines delineating regular radioopaque linear structures bordering the original joint space; and a subchondral bone plate reference line in the centre of said rectangular square, having a length corresponding to twice the width of the joint space; and
the landmark to determine the amount of normal joint space consists of joint space lines marking the translucent area bordered by two of said subchondral bone plate marking lines; and a joint space reference line having a length corresponding to the width of the joint space.

2. The measuring device according to claim 1, further comprising input means and computational means to determine as a fourth variable the width of the joint.

3. The device as claimed in claim 1 wherein the series of the at least two consecutive radiographs are taken within a time interval of at least six months.

4. The device as claimed in claim 1 wherein the interphalangeal finger joint is a distal and/or a proximal interphalangeal joint.

5. The device as claimed in claim 1 wherein the radiographs are digitized and the input means to select landmarks on said radiograph include manual or automatic input means.

6. The device according to claim 5, wherein the proportion of the subchondral bone area with normal-looking bone architecture within the landmark to determine the amount of normal tissue of the subchondral bone, is indicative for the amount of normal tissue of the subchondral bone.

7. The device according to claim 6, wherein the amount of normal tissue of the subchondral bone is computed using the following formula;

$$A_{sb}(\%) = 100 \times \frac{(1 - Pix_{[T \pm R]})}{\# Pix_{sq}}$$

wherein;
Asb=the area of subchondral bone tissue
Pix[T±R]=the amount of pixels having a pixel value equal to T±R, wherein T represents the translucent pixel value and R represents either the SEM of T or a predetermined deviation,
Pixsq=the total number of pixels found within the square of which the height equaled the width of the joint space, and wherein the joint space is positioned in the centre of said square.

8. The device according to claim 5, wherein the proportion of the subchondral bone plate marking lines within the subchondral bone plate reference line is indicative for the amount of normal tissue of the subchondral bone.

9. The device according to claim 8, wherein the amount of normal tissue of the subchondral bone plate is computed using the following formula:

$$A_{bp}(\%) = 100 \times \frac{(\# Pix_{sblm})}{\# Pix_{sbrl}}$$

wherein:
$A_{bp}$=the amount of normal subchondral bone plate,
$\#Pix_{sblm}$=the amount of pixels of the subchondral bone plate line marking
$\#Pix_{sbrl}$=the total number of pixels found within the subchondral bone plate reference line.

10. The device according to claim 5, wherein the proportion of the cumulative length of said joint space line markings within the length of said joint space reference line is indicative for the amount of a normal joint space.

11. The device according to claim 10, wherein the amount of normal joint space is computed using the following formula:

$$A_{js}(\%) = 100 \times \frac{(\#Pix_{tajs})}{\#Pix_{jsrl}}$$

wherein:
$A_{js}$=the amount of normal joint space
$\#Pix_{tajs}$=the amount of pixels of the joint space line markings
$\#Pix_{jsrl}$=the total number of pixels found within the joint space reference.

12. The device as claimed in claim 1 wherein the sum of the amount of normal tissue of the subchondral bone, the amount of normal tissue of the subchondral bone plate, and the amount of a normal joint space, gives an overall numerical score per interphalangeal finger joint of said subject.

13. The device according to claim 12, wherein the overall numerical score corresponds to: Total Score=$A_{sb}$=$A_{bp}$+$A_{js}$.

14. The device as claimed in claim 13 wherein a decrease in the overall numerical score is indicative for destruction of said interphalangeal finger joint and an increase in the overall numerical score is indicative for remodeling and repair of said interphalangeal finger joint.

15. Use of a device as claimed in claim 1 in a method to monitor natural disease progression in a subject with erosive osteoarthritis of the interphalangeal finger joints.

16. Use of a device as claimed in claim 1 in a method to identify or evaluate the effects of a drug in a subject with erosive osteoarthritis of the interphalangeal finger joints; in particular to determine whether the drug has anticatabolic or repair promoting effects.

17. Use of a device as claimed in claim 1 in a method to identify or evaluate a method of treatment for the subject with erosive osteoarthritis of the interphalangeal finger joints.

* * * * *